(12) United States Patent
de Godoy Lusso et al.

(10) Patent No.: US 10,945,393 B2
(45) Date of Patent: *Mar. 16, 2021

(54) HIGH YIELDING TOBACCO WITH ORIENTAL TOBACCO CHARACTERISTICS

(71) Applicant: Altria Client Services LLC, Richmond, VA (US)

(72) Inventors: Marcos Fernando de Godoy Lusso, Chesterfield, VA (US); Greg Davis, Midlothian, VA (US); Jerry W. Morris, Jetersville, VA (US)

(73) Assignee: Altria Client Services LLC, Richmond, VA (US)

( * ) Notice: Subject to any disclaimer, the term of this patent is extended or adjusted under 35 U.S.C. 154(b) by 79 days.

This patent is subject to a terminal disclaimer.

(21) Appl. No.: 16/259,406

(22) Filed: Jan. 28, 2019

(65) Prior Publication Data

US 2019/0150386 A1 May 23, 2019

Related U.S. Application Data

(63) Continuation of application No. 14/546,386, filed on Nov. 18, 2014, now Pat. No. 10,292,352.

(60) Provisional application No. 61/906,302, filed on Nov. 19, 2013, provisional application No. 61/915,617, filed on Dec. 13, 2013.

(51) Int. Cl.
| | |
|---|---|
| *A01H 5/12* | (2018.01) |
| *A01H 1/02* | (2006.01) |
| *A24B 13/00* | (2006.01) |
| *A24D 1/00* | (2020.01) |
| *C12N 5/04* | (2006.01) |
| *A24D 3/06* | (2006.01) |
| *A24B 9/00* | (2006.01) |
| *A24B 15/10* | (2006.01) |
| *A01H 6/82* | (2018.01) |

(52) U.S. Cl.
CPC ............... *A01H 5/12* (2013.01); *A01H 1/02* (2013.01); *A01H 6/823* (2018.05); *A24B 9/00* (2013.01); *A24B 13/00* (2013.01); *A24B 15/10* (2013.01); *A24D 1/00* (2013.01); *A24D 3/06* (2013.01); *C12N 5/04* (2013.01)

(58) Field of Classification Search
CPC ........... A24B 13/00; A24B 3/08; A24B 15/00; A24B 15/28; A01H 5/12; A01H 6/823; A01H 1/02; A01H 1/00; A01H 1/04
See application file for complete search history.

(56) References Cited

U.S. PATENT DOCUMENTS

| | | |
|---|---|---|
| 2,067,338 A | 1/1937 | Power et al. |
| 7,025,066 B2 | 4/2006 | Lawson et al. |
| 8,168,855 B2 | 5/2012 | Nielsen et al. |
| 2004/0084056 A1 | 5/2004 | Lawson et al. |
| 2006/0060211 A1 | 3/2006 | Conkling |
| 2006/0191548 A1 | 8/2006 | Strickland et al. |
| 2006/0236433 A1 | 10/2006 | Zaitlin et al. |
| 2008/0209586 A1 | 8/2008 | Nielsen et al. |
| 2008/0245377 A1 | 10/2008 | Marshall et al. |
| 2009/0119788 A1 | 5/2009 | Mallmann et al. |

FOREIGN PATENT DOCUMENTS

| | | |
|---|---|---|
| CN | 101084798 A | 12/2007 |
| EP | 0 419 188 A2 | 3/1991 |
| EP | 1 269 869 A1 | 1/2003 |
| GB | 2 460 499 A | 12/2009 |
| WO | WO 2004/041006 A1 | 5/2004 |
| WO | WO 2011/027315 A1 | 3/2011 |
| WO | WO 2014/078862 A1 | 5/2014 |

OTHER PUBLICATIONS

Matzinger et al (1968, Genetic diversity and heterosis in Nicotiana. II. Oriental X flue-cured variety crosses, Tobacco, vol. 12, pp. 177-180, XP009182449 published Sep. 27, 1968. In the IDS supplied by Applicant (Year: 1968).*
2013-2014 Kentucky & Tennessee Tobacco Production Guide, Lexington: Kentucky Cooperative Extension, pp. 2-67 (2013), In U.S. Appl. No. 14/546,386.
Ali, "The Quality Criteria of Oriental Tobacco Leaves Grown Under Dry Farming," *Journal of Zankoy Sulaimani*, 1(1):78-86 (1999), In U.S. Appl. No. 14/546,386.
Antoniou et al., Manual of Good Agriculture Practices for Oriental Tobacco, Thessaloniki: SEKE S.A., pp. 1-88 (2004), In U.S. Appl. No. 14/546,386.
Avery, Jr., "Structure and Germination of Tobacco Seed and the Developmental Anatomy of the Seedling Plant," *American Journal of Botany*, 20(5):309-327, (1933), In U.S. Appl. No. 14/546,386.
Chang et al., "Duvatrienediols in cuticular wax of Burley tobacco leaves," *Journal of Lipid Research*, 7:7-11 (1976), In U.S. Appl. No. 14/546,386.
Cox, The Chemical Analysis of Foods, London: J. & A. Churchill LTD., pp. 1-329 (1938), In U.S. Appl. No. 14/546,386.
Dagnon et al., "Evaluation of Aroma in Oriental Tobaccos as Based on Valeric Acid Gas Chromatography," *Contributions to Tobacco Research*, 23(2):115-120 (2008), In U.S. Appl. No. 14/546,386.
Dagnon et al., Chemometric Evaluation of the Colour and Smoke Aroma in Oriental Tobaccos Based on the Polyphenol and Valeric Acid Cultivar Characteristics as Influenced by the Genotype, *Bulgarian Journal of Argriculfrual Science*, 13:459-466 (2007), In U.S. Appl. No. 14/546,386.

(Continued)

*Primary Examiner* — Weihua Fan
(74) *Attorney, Agent, or Firm* — Arnold & Porter Kaye Scholer LLP

(57) ABSTRACT

This application provides high yielding tobacco plants with Oriental tobacco aroma and flavor characteristics and development of these plants via breeding. This application also provides hybrid seeds that give rise to high yielding tobacco plants with Oriental tobacco aroma and flavor characteristics. This application provides methods of growing and harvesting high yielding tobacco plants with Oriental tobacco aroma and flavor characteristics. This application further provides tobacco products made from high yielding tobacco plants with Oriental tobacco aroma and flavor characteristics, and methods making such tobacco products.

20 Claims, 1 Drawing Sheet

(56) References Cited

OTHER PUBLICATIONS

Fisher, Tobacco Blending, Chapter 11A, *Tobacco: Production, Chemistry and Technology*, edited by L. Davis and M. Nielsen, Blackwell Science, pp. 346-352 (1999), In U.S. Appl. No. 14/546,386.
Fricano et al., "Molecular diversity, population structure, and linkage disequilibrium in a worldwide collection of tobacco (*Nicotiana tabacum* L.) germplasm," BMC Genetics 13(1) 18 (2012), Herewith.
Gumus, "Economic Analysis of Oriental Tobacco in Turkey," *Bulg. J. Agric. Sci.*, 14(5):470-475 (2008), In U.S. Appl. No. 14/546,386.
Gwynn et al., "Inheritance of Sucrose Esters Containing β-Methylvaleric Acid in Tobacco," *Tobacco Science*, 29:79-81 (1985), In U.S. Appl. No. 14/546,386.
International Convention for the Protection of New Varieties of Plants, Nineteenth Extraordinary Session, Geneva pp. 1-8 (2002), In U.S. Appl. No. 14/546,386.
International Search Report and Written Opinion dated Feb. 19, 2015, as received in International Application No. PCT/US2014/066049, In U.S. Appl. No. 14/546,386.
Jones et al., "Performance of Tobacco Varieties in North Carolina," *Measured Crop Performance Tobacco 1963*, Research Report No. 9, pp. 1-74 (1963), In U.S. Appl. No. 14/546,386.
Khan et al., "Yield and Quality of Flue-Cured Virginia Tobacco, *Nicotiana tobacum* L. As Affected by Different Levels of Fico-Micron and Boron," *Sarhad J. Agric.*, 24(2):211-216 (2008), In U.S. Appl. No. 14/546,386.
Korubin-Aleksoska "Comparative Investigations of New Varieties of the Type Basmak with Popular Varieties of the Types Prilep, Yaka and Djebel," Tutun/Tobacco 65 (2015), Herewith.
Leffingwell et al., Tobacco Flavoring for Smoking Products, Winston-Salem: R. J. Reynolds Tobacco Company, pp. 1-72 (1972), In U.S. Appl. No. 14/546,386.
Leffingwell, "Basic Chemical Constituents of Tobacco Leaf and Differences among Tobacco Types," *Tobacco: Production, Chemistry, and Technology*, Blackwell Science, Chapter 8:265-284 (1999), In U.S. Appl. No. 14/546,386.
Lewis et al.,"Aspects of the evolution of *Nicotiana tabacum* L. and the status of the United States Nicotiana Germplasm Collection," *Genetic Resources and Crop Evolution*, 54(4)727-740 (2007), Herewith.
Matzinger et al., "Genetic Diversity and Heterosis in Nicotiana-D II Oriental X Flue Cured Variety Crosses," *Tobacco*, 12:177-180 (1968), In U.S. Appl. No. 14/546,386.
NC State University, 2013 Guide Flue-Cured Tobacco, Raleigh: North Carolina Cooperative Extension Service, pp. 2-212 (2013), In U.S. Appl. No. 14/546,386.
Nielsen et al., "Inheritance of a Diterpene Constituent in Tobacco Trichome Exudate," *Crop Science*, 32(5):1148-1150 (1992), In U.S. Appl. No. 14/546,386.
Nielsen et al., "Inheritance Pattern for Secreting and Nonsecreting Glandular Trichomes in Tobacco," *Crop Science*, 22(5):1051-1053 (1982), In U.S. Appl. No. 14/546,386.
Nielsen et al., "Variation of Flavor Components on Leaf Surfaces of Tobacco Genotypes Differing in Trichome Density," *J. Agic. Food Chem.*, 38(2):467-471 (1990), In U.S. Appl. No. 14/546,386.
Nielsen, "Aromatic Burley Tobaccos: Field Performance and Smoke Panel Evaluation," Tobacco Chemists' Research Conference, pp. 1 (1990), In U.S. Appl. No. 14/546,386.
Nugroho et al., "Secondary metabolism in tobacco," *Plant Cell, Tissue and Organ Culture*, Kluwer Academic Publishers, 68:105-125 (2002), In U.S. Appl. No. 14/546,386.

Philip Morris USA, "7 Appendix A: Overview of Smoke Chemistry," Version 1.0, pp. 69-91 (2001), In U.S. Appl. No. 14/546,386.
Sallaud et al., "Characterization of two genes for the biosynthesis of the labdane diterpene Z-abienol in tobacco (*Nicotiana tabacum*) glandular trichomes," *The Plant Journal*, Blackwell Publishing, 72:1-17 (2012), In U.S. Appl. No. 14/546,386.
Severson et al., "Isolation and Characterization of the Sucrose Esters of the Cuticular Waxes of Green Tobacco Leaf," *J. Agric. Food Chem.*, 33(5):870-875 (1985), In U.S. Appl. No. 14/546,386.
Severson et al., "Quantitation of the Major Cuticular Components from Green Leaf of Different Tobacco Types," *J. Agric. Food Chem.*, American Chemical Society, 32(3):566-570 (1984), In U.S. Appl. No. 14/546,386.
Severson, "The Cuticular Chemistry of N. Tabacum," *Journal of Agricultural Entomology*, 1(1): 34-42 (1984), In U.S. Appl. No. 14/546,386.
Sisson et al., "Inheritance of High Duvatrienol Production in Tobacco," *Tob. Sci.*, 37:25-29 (1993), In U.S. Appl. No. 14/546,386.
Smeeton, "Genetic Control of Tobacco Quality," *Recent Adv. Tob. Sci.*, 13:1-26 (1996), In U.S. Appl. No. 14/546,386.
Takeoka et al., "Volatile Constituents of Apricot (*Prunus armeniaca*)," *J. Agric. Food Chem.*, 38(2):471-477 (1990), In U.S. Appl. No. 14/546,386.
The "LC" Protocol, Version 2, pp. 1-23 (2007), In U.S. Appl. No. 14/546,386.
The University of Georgia College of Agricultural and Environmental Services, 2013 Georgia Tobacco Grower's Guide, Athens: The University of Georgia's Cooperative Extension Service, pp. 2-201 (2013), In U.S. Appl. No. 14/546,386.
Tomita et al., Inheritance of Labdanoid Producing Ability in *Nicotiana tabacum*, *Agric. Biol. Chem.*, 44(10):2517-2518 (1980), In U.S. Appl. No. 14/546,386.
Vann et al., "The Effect of Potassium Rate on the Yield and Quality of Flue-Cured Tobacco (*Nicotiana tabacum* L.)," *Tobacco Science*, 49:14-20 (2012), In U.S. Appl. No. 14/546,386.
Virginia Bright Flue-Cured Tobacco Board, 2012 Flue-Cured Tobacco Production Guide, Blacksburg: Virginia Cooperative Extension, pp. 1-132 (2012), In U.S. Appl. No. 14/546,386.
Vontimitta et al., "Analysis of a *Nicotiana tabacum* L. Genomic Region Controlling Two Leaf Surface Chemistry Traits," *J. Agric. Food Chem.*, 58:294-300 (2010), In U.S. Appl. No. 14/546,386.
Vontimitta, "Genetic Mapping of Genes Controlling Two Leaf Surface Trait Loci (QTL) Associated with Resistance to *Phytophthora nicotianae* in Tobacco (*Nicotiana tabacum* L.)," *Crop Science*, pp. 1-169 (2010), In U.S. Appl. No. 14/546,386.
Wang "Study on Difference and Genetic Character of Main Traits Among Different Types of *Nicotiana tabacum*, "Doctoral Dissertation, *Chinese Academy of Agricultural Sciences*, pp. 31-49 (2009), In U.S. Appl. No. 14/546,386.
Wernsman et al., "Tobacco," Chapter Seventeen, *Principles of Cultivar Development, Crop Species*, W. H. Fehr (ed.), MacMillan Publishing Co., Inc., New York, N.Y. 2:669-698 (1987), In U.S. Appl. No. 14/546,386.
Wolf "Turkish or Oriental Tobacco," *Economic Botany*, 3(1):32-41 (1949), Herewith.
Yang, et al. "Assessing the genetic diversity of tobacco germplasm using intersimple sequence repeat and interretrotransposon amplification polymorphism markers," *Annals of applied biology*, 150(3):393-401 (2007), Herewith.
Zhang et al., "Metabolic Profiling of Chinese Tobacco Leaf of Different Geographical Origins by GC-MC," *J. Agric. Food Chem.*, 61:2597-2605 (2013), In U.S. Appl. No. 14/546,386.

* cited by examiner

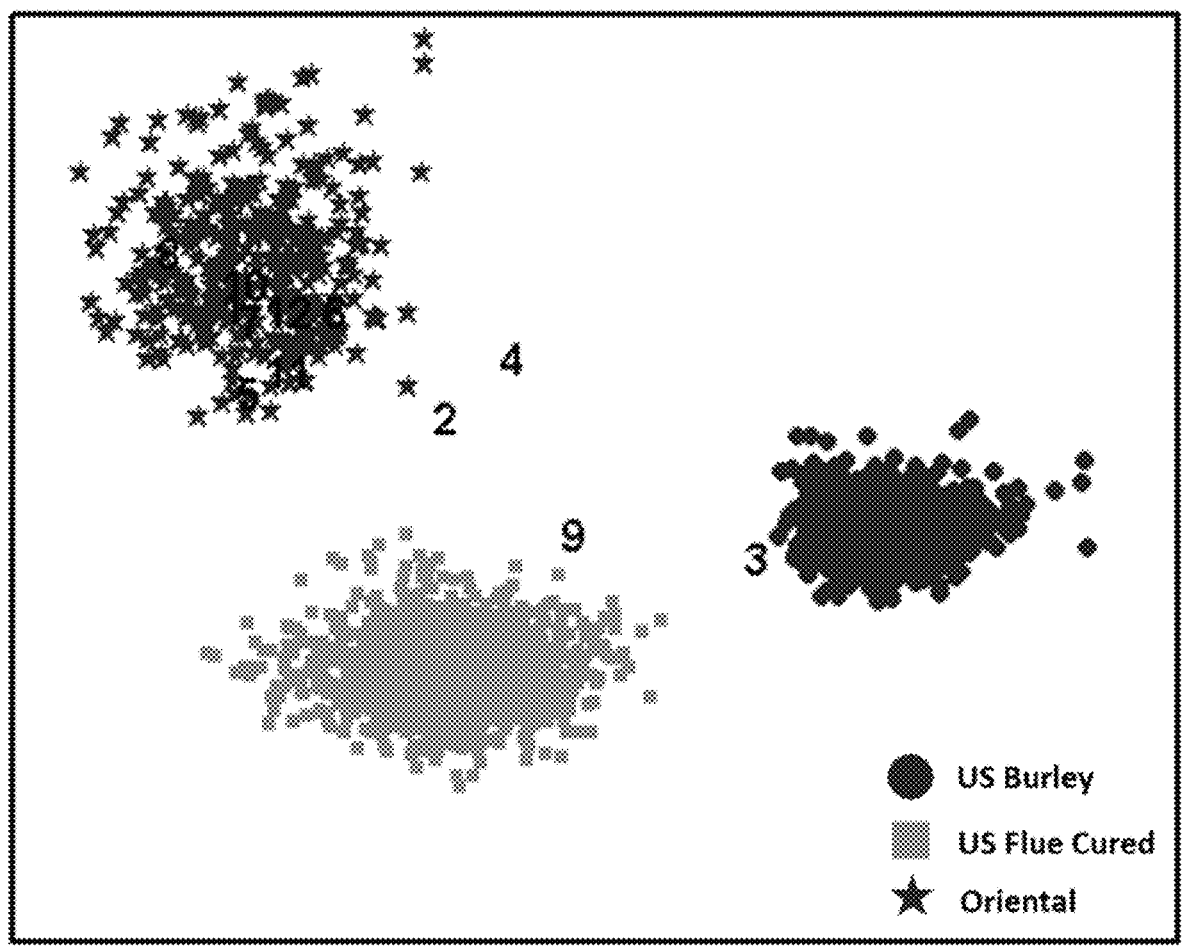

HIGH YIELDING TOBACCO WITH ORIENTAL TOBACCO CHARACTERISTICS

This application is a continuation of U.S. patent application Ser. No. 14/546,386, filed Nov. 18, 2014, which claims the benefit under 35 U.S.C. § 119(e) of U.S. Provisional Application Nos. 61/906,302, filed Nov. 19, 2013, and 61/915,617, filed Dec. 13, 2013, each of which are herein incorporated by reference in their entireties.

FIELD

The present disclosure provides high yielding tobacco plants with Oriental tobacco characteristics, their development via breeding, and production of tobacco products from these tobacco plants.

BACKGROUND

Different types of tobaccos are typically mixed at various ratios to form specific blends. For example, American-blend cigarettes are made with a mixture of flue-cured, Burley, and Oriental tobaccos. The specific percentage of each type varies from brand to brand, but generally contain 25-35% flue-cured, 25-35% air-cured Burley, 3-15% Oriental, 3-10% cut-rolled stem, and 10-25% reconstituted tobacco. See Fisher, Tobacco Blending, Chapter 11A, *Tobacco Production, Chemistry and Technology*, Edited by L. Davis and M. Nielsen, Blackwell Science, 1999. Organoleptic properties of different tobacco types vary considerably and are influenced by a complexity of factors including genetic differences, variations in cultural methods and curing practices, and environmental effects.

Traditional Oriental tobaccos are characterized by a unique aroma and flavor profile that is important for the production of blended cigarettes. These characteristics are the results of unique flavor and aroma compounds or the precursors for these compounds that are present at certain levels in the cured leaf. Some of the compounds associated with the flavor and aroma of Oriental tobacco smoke are: 3-methylvaleric acid, valeric acid, isovaleric acid, cembrenoid and labdenoid diterpenes, sugar esters, as well as others.

Another characteristic of traditional Oriental tobacco is the small leaf size (<8 inches). This small leaf size leads to a low yield per acre when compared to other tobacco types (e.g., flue-cured, Burley and dark tobaccos). Yield for the best quality Oriental tobacco is close to 600-800 lbs/acre while other tobacco types yield in the range of 2200 to 3500 lbs/acre. Major Oriental tobacco growing countries include Bulgaria, Greece, Macedonia, and Turkey.

Given the limited yields of typical Oriental varieties, there is a need to develop higher yielding tobacco types with Oriental tobacco characteristics. However, it is generally believed that such tobacco types are not achievable due to a negative relationship between tobacco yield and Oriental tobacco aroma characteristics. The instant disclosure overcomes this obstacle and provides such tobacco types which are hybrids between larger-leaf tobaccos and Oriental tobaccos. Among other advantages, the hybrid tobacco types provided in the instant disclosure can expand the cultivation of tobaccos with Oriental characteristics beyond the traditional Oriental growing regions. These hybrid Oriental tobacco types can also lead to lower production costs by potential mechanization of planting, harvesting, curing, and other production processes.

SUMMARY

The instant disclosure provides an F1 hybrid made between a larger-leaf parent tobacco plant with an Oriental parent tobacco plant, where the F1 hybrid comprises one or more Oriental aroma compounds at a concentration comparable to the concentration of those one of more Oriental aroma compounds in the Oriental parent of the F1 hybrid when grown under similar growth conditions. The instant disclosure provides non-naturally existing tobacco plants.

The instant disclosure also provides an F1 hybrid made between a larger-leaf parent tobacco plant with an Oriental parent tobacco plant, where the F1 hybrid comprises one or more compounds selected from the group consisting of 3-methylvaleric acid, valeric acid, isovaleric acid, a labdenoid, a cembrenoid, nicotine, total sugar esters, and reducing sugars at a concentration comparable to the concentration of those one or more compounds in the Oriental parent of the F1 hybrid when grown under similar growth conditions.

The instant disclosure further provides an F1 hybrid made between a flue-cured parent tobacco plant with an Oriental parent tobacco plant, where the F1 hybrid comprises one or more Oriental aroma compounds at a concentration comparable to the concentration of those one or more Oriental aroma compounds in the Oriental parent of the F1 hybrid, and the F1 hybrid further comprises one or more traits selected from the group consisting of mature plant height, harvestable leaf number, average node length, cutter leaf length, cutter leaf width, and yield comparable to those one or more traits in the flue-cured parent of the F1 hybrid when grown under similar growth conditions.

The instant disclosure also provides methods of producing, growing, and further breeding of an F1 hybrid disclosed herein.

The instant disclosure further provides cured tobaccos and tobacco products comprising tobacco material from an F1 hybrid disclosed herein. Tobacco products of the instant disclosure include, without limitation, cigarette products (e.g., cigarettes and bidi cigarettes), cigar products (e.g., cigar wrapping tobacco and cigarillos), pipe tobacco products, tobacco-derived nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, and the like. Tobacco products disclosed herein also include other smoking articles, particularly those smoking articles including filter elements, wherein the rod of smokable material includes cured tobacco within a tobacco blend.

Even further, the instant disclosure provides methods of manufacturing a tobacco product with tobacco material cured from an F1 hybrid disclosed herein.

BRIEF DESCRIPTION OF THE DRAWINGS

FIG. 1 shows spectral imaging profiles of sun-cured leaves from various tobacco varieties. A scatter plot is produced for Burley, flue-cured and Oriental tobacco types. A spectral fingerprint is established for each of candidate varieties 1 to 12 and plotted on the scatter plot. As shown, candidate varieties 1, 5 through 8, and 10 through 12 each fall within the range of Oriental fingerprints and exhibit the flavor and aroma characteristics of Oriental tobacco, while candidate varieties 2 through 4, and 9 do not. Tobacco hybrids K326×Basma (ID no. 7), K326×Katerini S53 (ID no. 8), and K326×Izmir Ego 64 (ID. no. 10) with spectral profiles typical of an Oriental tobacco.

DETAILED DESCRIPTION

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Any references cited herein are incorporated by reference in their entireties.

As used herein, the singular form "a," "an," and "the" include plural references unless the context clearly dictates otherwise. For example, the term "a compound" or "at least one compound" may include a plurality of compounds, including mixtures thereof.

The term "about" is used herein to mean approximately, roughly, around, or in the region of. When the term "about" is used in conjunction with a numerical range, it modifies that range by extending the boundaries above and below the numerical values set forth.

"Tobacco product" is defined as "any product made or derived from tobacco that is intended for human use or consumption, including any component, part, or accessory of a tobacco product (except for raw materials other than tobacco used in manufacturing a component, part, or accessory of a tobacco product)" (section 201 of the FD&C Act; 21 U.S.C. 321). The label and packaging is part of a tobacco product.

As used herein, larger-leaf tobaccos refer to tobacco types which produce leaves larger than leaves from traditional Oriental tobacco varieties. Larger-leaf tobaccos include, but are not limited to flue-cured tobaccos, air-cured tobaccos (e.g., Burley tobaccos, Maryland tobaccos, and dark air-cured tobaccos), dark fire-cured tobacco, and Galpao tobaccos.

Flue-cured tobaccos (also called Virginia or bright tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the U.S.

Air-cured tobaccos include Burley, Maryland, and dark tobaccos. The common factor is that curing is primarily without artificial sources of heat and humidity. Burley tobaccos are light to dark brown in color, high in oil, and low in sugar. Burley tobaccos are air-cured in barns. Major Burley growing countries are Argentina, Brazil, Italy, Malawi, and the U.S. Maryland tobaccos are extremely fluffy, has good burning properties, low nicotine and a neutral aroma. Major Maryland growing countries include the U.S. and Italy. Dark air-cured tobaccos are distinguished from other types primarily by its fermentation process which gives dark air-cured tobacco its medium- to dark-brown color and distinct aroma. Dark air-cured tobaccos are mainly used in the production of chewing tobacco and snuff.

Dark fire-cured tobaccos are generally dried with low-burning wood fires on the floors of closed curing barns. Their leaves have low sugar content but high nicotine content. Dark fire-cured tobaccos are used as a condimental for pipe blends, cigarettes, chewing tobacco, snuff and strong-tasting cigars. Major growing regions for dark fire-cured tobaccos are Tennessee, Kentucky, and Virginia, USA.

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant and leaf size, characteristic of today's Oriental varieties, as well as its unique aroma properties are a result of the plant's adaptation to the poor soil and stressful climatic conditions in which it develop over many past centuries.

Several factors such as environment, agronomic and curing practices and plant genetics can impact the level of aroma or flavor compounds in Oriental tobacco plants. Traditionally, the best quality Oriental tobacco leaves are produced in the Aegean Sea region in the countries of Turkey, Greece, Bulgaria and Macedonia. These countries have a mild, wet winter and spring and a hot, dry summer and fall. The dry and hot environment during the growing and curing season in this region offers the ideal conditions for high quality Oriental tobacco production. Best quality Oriental tobaccos are also produced in rocky, poor, somewhat infertile soil containing minimal amounts of nitrogen and organic matter. The most suitable terrains are generally sloping hillside fields or terraced lower mountainside locations with good drainage and ample direct sun. Among the practices used by growers in this region, little or no irrigation, low fertility, high plant population, harvesting method and sun curing have a direct impact on the Oriental tobacco leaf quality. An Oriental tobacco type as described in the instant disclosure can be selected to optimize effects on aroma or flavor compounds from environment, agronomic and curing practices and plant genetics factors.

Current Oriental tobacco varieties commercially produced in the Aegean Sea region are regional selections made by growers over many years. Farmer selection activities have led to varieties that are unique to the region where they are grown and that may have some distinct characteristics (e.g., Aroma and flavor profile, growing habits, regional adaptability, leaf yield, and the like).

Some of the current commercial Oriental varieties grown in different regions of the Aegean Sea have their names derived from the region where it is grown. Examples of these varieties are: Izmir, Katerini, Samsun, Basma and Krumovgrad. Other representative Oriental tobaccos include Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis and Balikesir tobaccos, as well as the so-called semi-Oriental tobaccos such as Sebinkarahisar, Borgka and East Balkan tobaccos. An Oriental plant of the instant disclosure can be from Oriental variety. Specific Oriental plants that may be used include, without limitation, those discussed herewith.

As mentioned above, without being limited by any scientific or biochemical theory, plant genetics can also impact the chemistry profile of the tobacco leaf including the compounds associated with aroma and flavor of Oriental tobacco. A number of studies aimed to understand the genetic controls for the production of main compounds associated with Oriental tobacco's smoke characteristics. For example, Tomita et al. reported that the cis-abienol production in tobacco variety Galpao No. 1 is genetically controlled by a single dominant gene. See Tomita et al., *Agric. Biol. Chem.*, 44 (10):2517-18 (1980). Analysis of the backcross populations and $F_2$ progenies of a cross between a cigar-filler type tobacco, TI 165 and a flue-cured tobacco, NC 2326 suggested that the production of β-methylvaleric acid (BMVSE) is controlled by a single dominant gene. See Gwynn et al., *Tobacco Science*, 29:79-81 (1985).

As used herein, Oriental aroma compounds are compounds associated with the flavor and aroma of Oriental tobacco smoke. These compounds include, but are not limited to, 3-methylvaleric acid, valeric acid, isovaleric acid, cembrenoid and labdenoid diterpenes, sugar esters. Concentrations of Oriental aroma compounds can be measured by any known metabolite profiling methods in the art including, without limitation, gas chromatography mass spectrometry (GC-MS), Nuclear Magnetic Resonance Spectroscopy, liquid chromatography-linked mass spectrometry. See The Handbook of Plant Metabolomics, edited by Weckwerth and Kahl, (Wiley-Blackwell) (May 28, 2013).

In one aspect, the instant disclosure provides an F1 hybrid tobacco plant, or part thereof, having a larger-leaf parent plant and an Oriental parent plant.

As used herein, an F1 hybrid tobacco plant is a tobacco plant resulting from a cross hybridization of two distinct parent plants. Two parent plants can be distinct in any aspect including, but not limited to, any quantitative differences or qualitative differences.

Tobacco parts provided herein include, but are not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In one aspect, the instant disclosure provides a tobacco cell that does not reproduce into a whole plant, for example, an endosperm cell.

As used herein, a larger-leaf parent plant may be from a larger-leaf inbred variety or a larger-leaf hybrid in which at least 50% of its nuclear DNA comes from one larger-leaf variety. In one aspect, a larger-leaf hybrid which is used as a larger-leaf parent plant herein, can comprise one or more segments of nuclear DNA introgressed from another variety, where greater than about 50%, 60%, 75%, 80%, 85%, 90%, 95%, 97%, or 99% of the nuclear DNA is DNA derived from one single larger-leaf variety.

As used herein, an Oriental parent plant may be from an Oriental inbred variety or an Oriental hybrid in which at least 50% of its nuclear DNA comes from one Oriental variety. In one aspect, an Oriental hybrid which is used as an Oriental parent plant herein, can comprise one or more segments of nuclear DNA introgressed from another variety, where greater than about 50%, 60%, 75%, 80%, 85%, 90%, 95%, 97%, or 99% of the nuclear DNA is DNA derived from one single Oriental variety.

In one aspect, the instant disclosure provides a population of F1 hybrid tobacco plants or other tobacco plants having a larger-leaf parent plant and an Oriental parent plant. In another aspect, the instant disclosure provides F1 hybrid tobacco seeds having a larger-leaf parent plant and an Oriental parent plant. In a further aspect, the instant disclosure provides a container of F1 hybrid tobacco seeds having a larger-leaf parent plant and an Oriental parent plant. Larger-leaf tobaccos of the instant disclosure include, but are not limited to flue-cured tobaccos, air-cured tobaccos, dark fire-cured tobaccos, and Galpao tobaccos.

In one aspect, the instant disclosure also provides an F1 hybrid tobacco plant, or part thereof, having a flue-cured parent plant and an Oriental type parent plant.

As used herein, a flue-cured parent plant may be from a flue-cured inbred variety or a flue-cured hybrid in which at least 50% of its nuclear DNA comes from one flue-cured variety. In one aspect, a flue-cured hybrid which is used as a flue-cured parent plant herein, can comprise one or more segments of nuclear DNA introgressed from another variety, where greater than about 50%, 60%, 75%, 80%, 85%, 90%, 95%, 97%, or 99% of the nuclear DNA is DNA derived from one single flue-cured variety.

In a further aspect, the instant disclosure provides a population of F1 hybrid tobacco plants or other tobacco plants having a flue-cured parent plant and an Oriental parent plant. In another aspect, the instant disclosure provides F1 hybrid tobacco seeds having a flue-cured parent plant and an Oriental parent plant. In a further aspect, the instant disclosure provides a container of F1 hybrid tobacco seeds having a flue-cured parent plant and an Oriental parent plant.

A container of F1 hybrid tobacco seeds of the instant disclosure may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Containers of tobacco seeds may be any container available in the art. By way of non-limiting example, a container may be a box, a bag, a packet, a pouch, a tape roll, a tube, or a bottle.

In one aspect, a population of F1 hybrid tobacco plants or other tobacco plants of the instant disclosure has a planting density of between about 5,000 and about 8000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of F1 hybrid tobacco plants or other tobacco plants of the instant disclosure is in a soil type with low to medium fertility.

In one aspect, F1 hybrid tobacco plants or seeds, or other tobacco plants or seeds of the instant disclosure have a flue-cured parent tobacco plant selected from the group consisting of CC 13, CC 27, CC 33, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. See NC State University, 2013 Guide FLUE-CURED TOBACCO, published by North Carolina Cooperative Extension Service. In another aspect, F1 hybrid tobacco plants or seeds, or other tobacco plants or seeds of the instant disclosure have a flue-cured parent tobacco plant selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1. In a further aspect, F1 hybrid tobacco plants or seeds, or other tobacco plants or seeds of the instant disclosure have a flue-cured parent tobacco plant from the variety K326.

In one aspect, F1 hybrid tobacco plants or seeds, or other tobacco plants or seeds of the instant disclosure have a flue-cured parent tobacco plant which is a hybrid and has at least 50% of its nuclear DNA comes from a flue-cured inbred variety selected from the group consisting of CC 13, CC 27, CC 33, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, and SPEIGHT 236. In another aspect, the flue-cured parent tobacco plant is a hybrid and has at least 50% of its nuclear DNA comes from a flue-cured inbred variety selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, and Va 182.

In one aspect, F1 hybrid tobacco plants or seeds, or other tobacco plants or seeds of the instant disclosure have an Oriental parent tobacco plant selected from the group consisting of Izmir, Katerini, Samsun, Basma and Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties. In another aspect, F1 hybrid tobacco plants or seeds, or other tobacco plants or seeds of the instant disclosure have an semi-Oriental parent tobacco plant selected from the group consisting of Sebinkarahisar, Borgka East Balkan, and any variety essentially derived from any one of the foregoing varieties. In a further aspect, F1 hybrid tobacco plants or seeds, or other tobacco plants or seeds of the instant disclosure have an Oriental parent tobacco selected from the group consisting of Basma, Katerini S53, and Izmir Ego 64.

In one aspect, an F1 hybrid tobacco plant of the instant disclosure is selected from the group consisting of MS K326×Izmir Ego 64, MS K326×Katerini S53 and MS K326×Basma.

As used herein, a dark air-cured parent plant may be from a dark air-cured inbred variety or a dark air-cured hybrid in which at least 50% of its nuclear DNA comes from one dark air-cured variety. In one aspect, a dark air-cured hybrid which is used as a dark air-cured parent plant herein, can comprise one or more segments of nuclear DNA introgressed from another variety, where greater than about 50%, 60%, 75%, 80%, 85%, 90%, 95%, 97%, or 99% of the nuclear DNA is DNA derived from one single dark air-cured variety.

As used herein, a Burley parent plant may be from a Burley inbred variety or a Burley hybrid in which at least 50% of its nuclear DNA comes from one Burley variety. In one aspect, a Burley hybrid which is used as a Burley parent plant herein, can comprise one or more segments of nuclear DNA introgressed from another variety, where greater than about 50%, 60%, 75%, 80%, 85%, 90%, 95%, 97%, or 99% of the nuclear DNA is DNA derived from one single Burley variety.

As used herein, a Maryland parent plant may be from a Maryland inbred variety or a Maryland hybrid in which at least 50% of its nuclear DNA comes from one Maryland variety. In one aspect, a Maryland hybrid which is used as a Maryland parent plant herein, can comprise one or more segments of nuclear DNA introgressed from another variety, where greater than about 50%, 60%, 75%, 80%, 85%, 90%, 95%, 97%, or 99% of the nuclear DNA is DNA derived from one single Maryland variety.

As used herein, a dark fire-cured parent plant may be from a dark fire-cured inbred variety or a dark fire-cured hybrid in which at least 50% of its nuclear DNA comes from one dark fire-cured variety. In one aspect, a dark fire-cured hybrid which is used as a dark fire-cured parent plant herein, can comprise one or more segments of nuclear DNA introgressed from another variety, where greater than about 50%, 60%, 75%, 80%, 85%, 90%, 95%, 97%, or 99% of the nuclear DNA is DNA derived from one single dark fire-cured variety.

In one aspect, F1 hybrid tobacco plants or seeds, or other tobacco plants or seeds of the instant disclosure have a dark air-cured parent tobacco plant selected from the group consisting of Sumatra, Jatim, Dominican Cubano, Besuki, One sucker, Green River, Virginia sun-cured, and Paraguan Passado. In another aspect, F1 hybrid tobacco plants or seeds, or other tobacco plants or seeds of the instant disclosure have a Burley parent tobacco plant selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, Bu 21×Ky 10, HB04P, Ky 14×L 8, Kt 200, Newton 98, Pedigo 561, Pf561 and Va 509. In a further aspect, F1 hybrid tobacco plants or seeds, or other tobacco plants or seeds of the instant disclosure have a Maryland parent tobacco plant selected from the group consisting of Md 10, Md 40, Md 201, Md 609, Md 872 and Md 341. In yet another aspect, F1 hybrid tobacco plants or seeds, or other tobacco plants or seeds of the instant disclosure have a dark fire-cured parent tobacco plant selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359. All foregoing mentioned specific varieties of dark air-cured, Burley, Maryland, or dark fire-cured type are only listed for exemplary purposes. Any additional dark air-cured, Burley, Maryland, or dark fire-cured varieties are also contemplated in the instant application.

In one aspect, an F1 hybrid tobacco plant or other tobacco plant of the instant disclosure comprise one or more Oriental aroma compounds at a concentration comparable to the concentration of the same one or more Oriental aroma compounds in the Oriental parent of the F1 hybrid, when grown under similar growth conditions. In another aspect, the concentrations of one or more Oriental aroma compounds in an F1 hybrid tobacco plant or other tobacco plant are about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the concentrations of the one or more Oriental aroma compounds in the Oriental parent of the F1 hybrid when grown in similar field conditions. In a further aspect, an Oriental aroma compound is selected from the group consisting of 3-methylvaleric acid, valeric acid, isovaleric acid, a labdenoid, a cembrenoid, a sugar ester, and a reducing sugar.

In one aspect, an F1 hybrid tobacco plant or other tobacco plant of the instant disclosure comprise 3-methylvaleric acid at a concentration comparable to the 3-methylvaleric acid concentration in the Oriental parent of the F1 hybrid when grown under similar growth conditions. In a further aspect, the 3-methylvaleric acid concentration in an F1 hybrid tobacco plant or other tobacco plant is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the 3-methylvaleric acid concentration in the Oriental parent of the F1 hybrid. In a further aspect, the 3-methylvaleric acid concentration is measured from cured tobacco leaves. In another aspect, the 3-methylvaleric acid concentration is measured from sun-cured tobacco leaves.

In a further aspect, an F1 hybrid tobacco plant or other tobacco plant of the instant disclosure comprise 3-methylvaleric acid at a concentration selected from the group consisting of about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1650, about 1700, about 1750, about 1800, about 1850, about 1900, about 1950, about 2000, about 2050, about 2100, about 2150, about 2200, about 2250, about 2300, about 2350, about 2400, about 2450, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, and about 5000 µg/g.

In one aspect, an F1 hybrid tobacco plant or other tobacco plant of the instant disclosure comprise valeric acid at a concentration comparable to the valeric acid concentration in the Oriental parent of the F1 hybrid when grown under similar growth conditions. In a further aspect, the valeric acid concentration in an F1 hybrid tobacco plant or other tobacco plant is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the valeric acid concentration in the Oriental parent of the F1 hybrid. In a further aspect, the valeric acid concentration is measured from cured tobacco leaves. In another aspect, the valeric acid concentration is measured from sun-cured tobacco leaves.

In a further aspect, an F1 hybrid tobacco plant or other tobacco plant of the instant disclosure comprise valeric acid at a concentration selected from the group consisting of about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1650, about 1700, about 1750, about 1800, about 1850, about 1900, about 1950, about 2000, about 2050, about 2100, about 2150, about 2200, about 2250, about 2300, about 2350, about 2400, about 2450, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, and about 5000 µg/g.

In one aspect, an F1 hybrid tobacco plant or other tobacco plant of the instant disclosure comprise isovaleric acid at a concentration comparable to the isovaleric acid concentration in the Oriental parent of the F1 hybrid when grown under similar growth conditions. In a further aspect, the isovaleric acid concentration in an F1 hybrid tobacco plant or other tobacco plant is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the isovaleric acid concentration in the Oriental parent of the F1 hybrid. In a further aspect, the isovaleric acid concentration is measured from cured tobacco leaves. In another aspect, the isovaleric acid concentration is measured from sun-cured tobacco leaves.

In a further aspect, an F1 hybrid tobacco plant or other tobacco plant of the instant disclosure comprise valeric acid at a concentration selected from the group consisting of about 200, about 225, about 250, about 275, about 300, about 325, about 350, about 375, about 400, about 425, about 450, about 475, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1650, about 1700, about 1750, about 1800, about 1850, about 1900, about 1950, and about 2000 µg/g.

In one aspect, an F1 hybrid tobacco plant or other tobacco plant of the instant disclosure comprise a labdenoid at a concentration comparable to the labdenoid concentration in the Oriental parent of the F1 hybrid when grown under similar growth conditions. In a further aspect, the labdenoid concentration in an F1 hybrid tobacco plant or other tobacco plant is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the labdenoid concentration in the Oriental parent of the F1 hybrid. In another aspect, the labdenoid is cis-abienol. In a further aspect, the labdenoid concentration is measured from green leaves.

In a further aspect, an F1 hybrid tobacco plant or other tobacco plant of the instant disclosure comprise cis-abienol at a concentration selected from the group consisting of about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, and about 50 mg/cm$^2$.

In one aspect, an F1 hybrid tobacco plant or other tobacco plant of the instant disclosure comprise a cembrenoid at a concentration comparable to the cembrenoid concentration in the Oriental parent of the F1 hybrid when grown under similar growth conditions. In a further aspect, the cembrenoid concentration in an F1 hybrid tobacco plant or other tobacco plant is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the cembrenoid concentration in the Oriental parent of the F1 hybrid. In another aspect, the cembrenoid is duvatrienediols. In a further aspect, the cembrenoid concentration is measured from green leaves.

In a further aspect, an F1 hybrid tobacco plant or other tobacco plant of the instant disclosure comprise duvatrienediols at a concentration selected from the group consisting of about 100, about 125, about 150, about 175, about 200, about 225, about 250, about 275, about 300, about 325, about 350, about 375, about 400, about 425, about 450, about 475, about 500, about 550, about 600, about 650, about 700, about 750, and about 800 mg/cm$^2$.

In one aspect, an F1 hybrid tobacco plant or other tobacco plant of the instant disclosure comprise total sugar esters (III to V) at a concentration comparable to the total sugar ester concentration in the Oriental parent of the F1 hybrid when grown under similar growth conditions. In a further aspect, the total sugar ester concentration in an F1 hybrid tobacco plant or other tobacco plant is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the total sugar ester concentration in the Oriental parent of the F1 hybrid. In a further aspect, the total sugar ester concentration is measured from green leaves.

In a further aspect, an F1 hybrid tobacco plant or other tobacco plant of the instant disclosure comprise total sugar esters (III to V) at a concentration selected from the group consisting of about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120, about 130, about 140, about 150, about 160, about 170, about 180, about 190, and about 200 mg/cm$^2$.

In one aspect, an F1 hybrid tobacco plant or other tobacco plant of the instant disclosure comprise reducing sugars at a concentration comparable to the reducing sugar concentration in the Oriental parent of the F1 hybrid when grown under similar growth conditions. Reducing sugar contents can be determined in any method, for example, a titration method (e.g., the Lane-Eynon method), or a gravimetric method (e.g., the Munson and Walker method).

In a further aspect, the reducing sugar concentration in an F1 hybrid tobacco plant or other tobacco plant is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the reducing sugar concentration in the Oriental parent of the F1 hybrid. In a further aspect, the reducing sugar concentration is measured from cured tobacco leaves. In another aspect, the reducing sugar concentration is measured from sun-cured tobacco leaves.

In a further aspect, cured leaves from an F1 hybrid tobacco plant or other tobacco plant of the instant disclosure comprise a reducing sugar content selected from the group consisting of about 1%, about 2%, about 3%, about 4%, about 5%, about 6%, about 7%, about 8%, about 9%, about 10%, about 11%, about 12%, about 13%, about 14%, about 15%, about 16%, about 17, about 18%, about 19%, about 20%, about 21%, about 22%, about 23%, about 24%, about 25%, about 26%, about 27%, about 28%, about 29%, and about 30%.

In one aspect, an F1 hybrid tobacco plant or other tobacco plant of the instant disclosure comprise nicotine at an average concentration comparable to the average nicotine concentration in the Oriental parent of the F1 hybrid when grown under similar growth conditions. Nicotine can be measured by using any method available in the art. See Analytical Determination of Nicotine and Related Compounds and Their Metabolites, edited by Gorrod and Jacob (1999).

In a further aspect, the average nicotine concentration in an F1 hybrid tobacco plant or other tobacco plant is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the average nicotine concentration in the Oriental parent of the F1 hybrid. In a further aspect, the nicotine concentration is measured from cured tobacco leaves. In another aspect, the nicotine concentration is measured from sun-cured tobacco leaves.

In one aspect, the average nicotine concentration in an F1 hybrid tobacco plant or other tobacco plant of the instant disclosure is selected from the group consisting of between about 0.5% and about 3%, between about 0.6% and about 2.9%, between about 0.7% and about 2.8%, between about 0.8% and about 2.7%, between about 0.9% and about 2.6%, between about 1.0% and about 2.5%, between about 1.1% and about 2.4%, between about 1.2% and about 2.3%, between about 1.3% and about 2.2%, between about 1.4% and about 2.1%, between about 1.5% and about 2.0%, between about 1.6% and about 1.9%, and between about 1.7% and about 1.8%.

In another aspect, the average nicotine concentration in an F1 hybrid tobacco plant or other tobacco plant of the instant disclosure is selected from the group consisting of between about 0.5% and about 3%, between about 0.6% and about 3%, between about 0.7% and about 3%, between about 0.8% and about 3%, between about 0.9% and about 3%, between about 1.0% and about 3%, between about 1.1% and about 3%, between about 1.2% and about 3%, between about 1.3% and about 3%, between about 1.4% and about 3%, between about 1.5% and about 3%, between about 1.6% and about 3%, between about 1.7% and about 3%, between about 1.8% and about 3%, between about 1.9% and about 3%, between about 2.0% and about 3%, between about 2.1% and about 3%, between about 2.2% and about 3%, between about 2.3% and about 3%, between about 2.4% and about 3%, between about 2.5% and about 3%, between about 2.6% and about 3%, and between about 2.7% and about 3%.

In a further aspect, the average nicotine concentration in an F1 hybrid tobacco plant or other tobacco plant of the instant disclosure is selected from the group consisting of between about 0.5% and about 3%, between about 0.5% and about 2.9%, between about 0.5% and about 2.8%, between about 0.5% and about 2.7%, between about 0.5% and about 2.6%, between about 0.5% and about 2.5%, between about 0.5% and about 2.4%, between about 0.5% and about 2.3%, between about 0.5% and about 2.2%, between about 0.5% and about 2.1%, between about 0.5% and about 2.0%, between about 0.5% and about 1.9%, between about 0.5% and about 1.8%, between about 0.5% and about 1.7%, between about 0.5% and about 1.6%, between about 0.5% and about 1.5%, between about 0.5% and about 1.4%, between about 0.5% and about 1.3%, between about 0.5% and about 1.2%, between about 0.5% and about 1.1%, and between about 0.5% and about 1.0%.

An F1 hybrid of the instant disclosure can also comprises one or more traits selected from the group consisting of mature plant height, harvestable leaf number, average node length, cutter leaf length, cutter leaf width, and yield comparable to those one or more traits in the larger-leaf parent of the F1 hybrid when grown under similar growth conditions.

In one aspect, an F1 hybrid tobacco plant or other tobacco plant of the instant disclosure comprise a mature plant height close to or higher than the average mature plant height of the flue-cured parent of the F1 hybrid, when grown in similar field conditions. In another aspect, the mature plant height of an F1 hybrid tobacco plant or other tobacco plant is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, between 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the mature plant height of the flue-cured parent of the F1 hybrid, when grown in similar field conditions.

In another aspect, the mature plant height of an F1 hybrid tobacco plant or other tobacco plant is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the mature plant height of the Oriental parent of the F1 hybrid, when grown in similar field conditions.

In one aspect, the mature plant height of an F1 hybrid tobacco plant or other tobacco plant is between about 30 and about 65 inches, between about 32.5 and about 62.5 inches, between about 35 and about 60 inches, between about 37.5 and about 57.5 inches, between about 40 and about 55 inches, between about 42.5 and about 52.5 inches, and between about 45 and about 50 inches.

In another aspect, the mature plant height of an F1 hybrid tobacco plant or other tobacco plant is between about 30 and about 100 inches, between about 32.5 and about 100 inches, between about 35 and about 100 inches, between about 37.5 and about 100 inches, between about 40 and about 100 inches, between about 42.5 and about 100 inches, between about 45 and about 100 inches, between about 47.5 and about 100 inches, between about 50 and about 100 inches, between about 52.5 and about 100 inches, between about 55 and about 100 inches, between about 65 and about 100 inches, between about 67.5 and about 100 inches, between about 70 and about 100 inches, between about 72.5 and about 100 inches, between about 75 and about 100 inches, between 77.5 and about 100 inches, between about 80 and about 100 inches, between about 82.5 and about 100 inches, between about 85 and about 100 inches, between about 87.5 and about 100 inches, between about 90 and about 100 inches, between about 92.5 and about 100 inches, between about 95 and about 100 inches, and between about 97.5 and about 100 inches.

In a further aspect, the mature plant height of an F1 hybrid tobacco plant or other tobacco plant is between about 30 to about 100 inches, between about 30 to about 97.5 inches, between about 30 and about 95 inches, between about 30 and about 92.5 inches, between about 30 and about 90 inches, between about 30 and 87.5 inches, between about 30 and about 85 inches, between about 30 and about 82.5 inches, between about 30 and about 80 inches, between about 30 and about 77.5 inches, between about 30 and about 75 inches, between about 30 and about 72.5 inches, between about 30 and about 70 inches, between about 30 and about 67.5 inches, between about 30 and about 65 inches, between about 30 and about 62.5 inches, between about 30 and about 60 inches, between about 30 and about 57.5 inches, between about 30 and about 55 inches, between about 30 and about 52.5 inches, between about 30 and about 50 inches, between about 30 and about 47.5 inches, between about 30 and about 45 inches, between about 30 and about 42.5 inches, between about 30 and about 40 inches, between about 30 and about 37.5 inches, and between about 30 and about 35 inches. Mature plant height of a hybrid tobacco plant mentioned herein is measured from a plant without topping. In one aspect, an F1 hybrid tobacco plant or other tobacco plant of the instant disclosure is grown and harvested without topping.

In one aspect, an F1 hybrid tobacco plant or other tobacco plant of the instant disclosure comprise at maturation a similar number of harvestable leaves compared to the flue-cured parent of the F1 hybrid when grown in similar field conditions. In another aspect, an F1 hybrid tobacco plant or other tobacco plant of the instant disclosure comprise at maturation a similar number of harvestable leaves compared to the Oriental parent of the F1 hybrid when grown in similar field conditions.

In one aspect, the number of harvestable leaves in an F1 hybrid tobacco plant or other tobacco plant of the instant disclosure is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the number of harvestable leaves in the Oriental parent or the flue-cured parent of the F1 hybrid when grown in similar field conditions.

In one aspect, the number of harvestable leaves at maturation in an F1 hybrid tobacco plant or other tobacco plant of the instant disclosure is selected from the group consisting of between about 12 and about 40, between about 14 and about 38, between about 16 and about 36, between about 18 and about 34, between about 20 and about 32, between about 22 and about 30, and between about 24 and about 28.

In another aspect, the number of harvestable leaves at maturation in an F1 hybrid tobacco plant or other tobacco plant of the instant disclosure is selected from the group consisting of between about 12 and about 40, between about 14 and about 40, between about 16 and about 40, between about 18 and about 40, between about 20 and about 40, between about 22 and about 40, between about 24 and about 40, between about 26 and about 40, between about 28 and about 40, between about 30 and about 40, between about 32 and about 40, between about 34 and about 40, and between about 36 and about 40.

In a further aspect, the number of harvestable leaves at maturation in an F1 hybrid tobacco plant or other tobacco plant of the instant disclosure is selected from the group consisting of between about 12 and about 40, between about 12 and about 38, between about 12 and about 36, between about 12 and about 34, between about 12 and about 32, between about 12 and about 30, between about 12 and about 28, between about 12 and about 26, between about 12 and about 24, between about 12 and about 22, between about 12 and about 20, between about 12 and about 18, and between about 12 and about 16.

In one aspect, an F1 hybrid tobacco plant or other tobacco plant of the instant disclosure comprise at maturation a similar average node length compared to the flue-cured parent of the F1 hybrid when grown in similar field conditions. In another aspect, an F1 hybrid tobacco plant or other tobacco plant of the instant disclosure comprise at maturation a similar average node length compared to the Oriental parent of the F1 hybrid when grown in similar field conditions.

In one aspect, the average node length in an F1 hybrid tobacco plant or other tobacco plant of the instant disclosure is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the average node length in the Oriental parent or the flue-cured parent of the F1 hybrid when grown in similar field conditions.

In one aspect, the average node length at maturation in an F1 hybrid tobacco plant or other tobacco plant of the instant disclosure is selected from the group consisting of between about 0.5 and about 3 inches, between about 0.6 and about 2.9 inches, between about 0.7 and about 2.8 inches, between about 0.8 and about 2.7 inches, between about 0.9 and about 2.6 inches, between about 1.0 and about 2.5 inches, between about 1.1 and about 2.4 inches, between about 1.2 and about 2.3 inches, between about 1.3 and about 2.2 inches, between about 1.4 and about 2.1 inches, between about 1.5 and about 2.0 inches, between about 1.6 and about 1.9 inches, and between about 1.7 and about 1.8 inches.

In another aspect, the average node length at maturation in an F1 hybrid tobacco plant or other tobacco plant of the instant disclosure is selected from the group consisting of between about 0.5 and about 3 inches, between about 0.6 and about 3 inches, between about 0.7 and about 3 inches, between about 0.8 and about 3 inches, between about 0.9 and about 3 inches, between about 1.0 and about 3 inches, between about 1.1 and about 3 inches, between about 1.2 and about 3 inches, between about 1.3 and about 3 inches, between about 1.4 and about 3 inches, between about 1.5 and about 3 inches, between about 1.6 and about 3 inches, between about 1.7 and about 3 inches, between about 1.8 and about 3 inches, between about 1.9 and about 3 inches, between about 2.0 and about 3 inches, between about 2.1 and about 3 inches, between about 2.2 and about 3 inches, between about 2.3 and about 3 inches, between about 2.4 and about 3 inches, between about 2.5 and about 3 inches, between about 2.6 and about 3 inches, and between about 2.7 and about 3 inches.

In a further aspect, the average node length at maturation in an F1 hybrid tobacco plant or other tobacco plant of the instant disclosure is selected from the group consisting of between about 0.5 and about 3 inches, between about 0.5 and about 2.9 inches, between about 0.5 and about 2.8 inches, between about 0.5 and about 2.7 inches, between about 0.5 and about 2.6 inches, between about 0.5 and about 2.5 inches, between about 0.5 and about 2.4 inches, between about 0.5 and about 2.3 inches, between about 0.5 and about 2.2 inches, between about 0.5 and about 2.1 inches, between about 0.5 and about 2.0 inches, between about 0.5 and about 1.9 inches, between about 0.5 and about 1.8 inches, between about 0.5 and about 1.7 inches, between about 0.5 and about 1.6 inches, between about 0.5 and about 1.5 inches, between about 0.5 and about 1.4 inches, between about 0.5 and about 1.3 inches, between about 0.5 and about 1.2 inches, between about 0.5 and about 1.1 inches, and between about 0.5 and about 1.0 inches.

In one aspect, an F1 hybrid tobacco plant or other tobacco plant of the instant disclosure comprise cutters at maturation at a similar size compared to cutters from the flue-cured parent of the F1 hybrid when grown in similar field conditions. In another aspect, an F1 hybrid tobacco plant or other tobacco plant of the instant disclosure comprise cutters at maturation at a similar size compared to cutters from the Oriental parent of the F1 hybrid when grown in similar field conditions. Cutters are the largest leaves on a tobacco plant, both in length and width. Tobacco stock positions include 1st stalk position (also called primings or sand lugs), 2nd stalk position (also called lugs), 3rd stalk position (also called cutters), 4th stalk position (also called leaf), 5th stalk position (also called smoking leaf), and 6th stalk position (also called tips).

In one aspect, the length of cutters in an F1 hybrid tobacco plant or other tobacco plant of the instant disclosure is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the length of cutters in the Oriental parent or the flue-cured parent of the F1 hybrid when grown in similar field conditions.

In one aspect, the cutters from an F1 hybrid tobacco plant or other tobacco plant of the instant disclosure have an average length at maturation selected from the group consisting of between about 14 and about 44 inches, between about 16 and about 42 inches, between about 16 and about 40 inches, between about 17 and about 38 inches, between about 18 and about 36 inches, between about 19 and about 34 inches, between about 20 and about 32 inches, between about 21 and about 30 inches, between about 22 and about 28 inches, and between about 23 and about 26 inches.

In another aspect, the cutters from an F1 hybrid tobacco plant or other tobacco plant of the instant disclosure have an average length at maturation selected from the group consisting of between about 14 and about 44 inches, between about 16 and about 44 inches, between about 16 and about 44 inches, between about 17 and about 44 inches, between about 18 and about 44 inches, between about 19 and about 44 inches, between about 20 and about 44 inches, between about 21 and about 44 inches, between about 22 and about 44 inches, between about 23 and about 44 inches, between about 24 and about 44 inches, between about 25 and about 44 inches, between about 26 and about 44 inches, between about 27 and about 44 inches, between about 28 and about 44 inches, between about 29 and about 44 inches, and between about 30 and about 44 inches.

In a further aspect, the cutters from an F1 hybrid tobacco plant or other tobacco plant of the instant disclosure have an average length at maturation selected from the group consisting of between about 14 and about 44 inches, between about 14 and about 42 inches, between about 14 and about 40 inches, between about 14 and about 38 inches, between about 14 and about 36 inches, between about 14 and about 34 inches, between about 14 and about 32 inches, between about 14 and about 30 inches, between about 14 and about 28 inches, between about 14 and about 26 inches, between about 14 and about 24 inches, between about 14 and about 22 inches, between about 14 and about 20 inches, and between about 14 and about 18 inches.

In one aspect, the width of cutters in an F1 hybrid tobacco plant or other tobacco plant of the instant disclosure is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the width of cutters in the Oriental parent or the flue-cured parent of the F1 hybrid when grown in similar field conditions.

In one aspect, the cutters from an F1 hybrid tobacco plant or other tobacco plant of the instant disclosure have an average width at maturation selected from the group consisting of between about 8 and about 22 inches, between about 9 and about 21 inches, between about 10 and about 20 inches, between about 11 and about 18 inches, between about 12 and about 16 inches, and between about 13 and about 15 inches.

In another aspect, the cutters from an F1 hybrid tobacco plant or other tobacco plant of the instant disclosure have an average width at maturation selected from the group consisting of between about 8 and about 22 inches, between about 9 and about 22 inches, between about 10 and about 22 inches, between about 11 and about 22 inches, between about 12 and about 22 inches, between about 13 and about 22 inches, between about 14 and about 22 inches, between about 15 and about 22 inches, between about 16 and about 22 inches, between about 17 and about 22 inches, between about 18 and about 22 inches, between about 19 and about 22 inches, and between about 20 and about 22 inches.

In a further aspect, the cutters from an F1 hybrid tobacco plant or other tobacco plant of the instant disclosure have an average width at maturation selected from the group consisting of between about 8 and about 22 inches, between about 8 and about 21 inches, between about 8 and about 20 inches, between about 8 and about 18 inches, between about 8 and about 16 inches, between about 8 and about 15 inches, between about 8 and about 14 inches, between about 8 and about 13 inches, between about 8 and about 12 inches, between about 8 and about 11 inches, and between about 8 and about 10 inches.

In one aspect, an F1 hybrid tobacco plant or other tobacco plant of the instant disclosure comprise a 10th leaf from bottom at maturation at a similar size compared to a 10th leaf from bottom from the flue-cured parent of the F1 hybrid when grown in similar field conditions. In another aspect, an F1 hybrid tobacco plant or other tobacco plant of the instant disclosure comprise a 10th leaf from bottom at maturation at a similar size compared to a 10th leaf from bottom from the Oriental parent of the F1 hybrid when grown in similar field conditions.

In one aspect, the length of a 10th leaf from bottom in an F1 hybrid tobacco plant or other tobacco plant of the instant disclosure is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the length of a 10th leaf from bottom in the Oriental parent or the flue-cured parent of the F1 hybrid when grown in similar field conditions.

In one aspect, a 10th leaf from bottom from an F1 hybrid tobacco plant or other tobacco plant of the instant disclosure have an average length at maturation selected from the group consisting of between about 14 and about 44 inches, between about 16 and about 42 inches, between about 16 and about 40 inches, between about 17 and about 38 inches, between about 18 and about 36 inches, between about 19 and about 34 inches, between about 20 and about 32 inches, between about 21 and about 30 inches, between about 22 and about 28 inches, and between about 23 and about 26 inches.

In another aspect, a 10th leaf from bottom from an F1 hybrid tobacco plant or other tobacco plant of the instant disclosure have an average length at maturation selected from the group consisting of between about 14 and about 44 inches, between about 16 and about 44 inches, between about 16 and about 44 inches, between about 17 and about 44 inches, between about 18 and about 44 inches, between about 19 and about 44 inches, between about 20 and about 44 inches, between about 21 and about 44 inches, between about 22 and about 44 inches, between about 23 and about 44 inches, between about 24 and about 44 inches, between about 25 and about 44 inches, between about 26 and about 44 inches, between about 27 and about 44 inches, between about 28 and about 44 inches, between about 29 and about 44 inches, and between about 30 and about 44 inches.

In a further aspect, a 10th leaf from bottom from an F1 hybrid tobacco plant or other tobacco plant of the instant disclosure have an average length at maturation selected from the group consisting of between about 14 and about 44 inches, between about 14 and about 42 inches, between about 14 and about 40 inches, between about 14 and about 38 inches, between about 14 and about 36 inches, between about 14 and about 34 inches, between about 14 and about 32 inches, between about 14 and about 30 inches, between about 14 and about 28 inches, between about 14 and about 26 inches, between about 14 and about 24 inches, between about 14 and about 22 inches, between about 14 and about 20 inches, and between about 14 and about 18 inches.

In one aspect, the width of a 10th leaf from bottom in an F1 hybrid tobacco plant or other tobacco plant of the instant disclosure is about between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the width of a 10th leaf from bottom in the Oriental parent or the flue-cured parent of the F1 hybrid when grown in similar field conditions.

In one aspect, a 10th leaf from bottom from an F1 hybrid tobacco plant or other tobacco plant of the instant disclosure have an average width at maturation selected from the group consisting of between about 8 and about 22 inches, between about 9 and about 21 inches, between about 10 and about 20 inches, between about 11 and about 18 inches, between about 12 and about 16 inches, and between about 13 and about 15 inches.

In another aspect, a 10th leaf from bottom from an F1 hybrid tobacco plant or other tobacco plant of the instant disclosure have an average width at maturation selected from the group consisting of between about 8 and about 22 inches, between about 9 and about 22 inches, between about 10 and about 22 inches, between about 11 and about 22 inches, between about 12 and about 22 inches, between about 13 and about 22 inches, between about 14 and about 22 inches, between about 15 and about 22 inches, between about 16 and about 22 inches, between about 17 and about 22 inches, between about 18 and about 22 inches, between about 19 and about 22 inches, and between about 20 and about 22 inches.

In a further aspect, a 10th leaf from bottom from an F1 hybrid tobacco plant or other tobacco plant of the instant disclosure have an average width at maturation selected from the group consisting of between about 8 and about 22 inches, between about 8 and about 21 inches, between about 8 and about 20 inches, between about 8 and about 18 inches, between about 8 and about 16 inches, between about 8 and about 15 inches, between about 8 and about 14 inches, between about 8 and about 13 inches, between about 8 and about 12 inches, between about 8 and about 11 inches, and between about 8 and about 10 inches.

In one aspect, an F1 hybrid tobacco plant or other tobacco plant of the instant disclosure comprise a yield similar to the yield of the flue-cured type parent variety of the F1 hybrid when grown in similar field conditions.

Unless specified otherwise, used herein, tobacco yield refers to cured leaf yield which is calculated based on the weight of cured tobacco leaves per acre under standard field conditions following standard agronomic and curing practice.

In one aspect, an F1 hybrid tobacco plant or other tobacco plant of the instant disclosure has a yield between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the yield of the flue-cured parent of the F1 hybrid when grown in similar field conditions. In another aspect, the yield of an F1 hybrid tobacco plant or other tobacco plant of the instant disclosure is approximately 1.5, 1.6, 1.7, 1.8, 1.9, 2.0, 2.1, 2.2, 2.3, 2.4, 2.5, 2.6, 2.7, 2.8, 2.9, or 3.0 times of the yield of the Oriental parent of the F1 hybrid when grown in similar field conditions.

In one aspect, an F1 hybrid tobacco plant or other tobacco plant of the instant disclosure provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre.

In another aspect, an F1 hybrid tobacco plant or other tobacco plant of the instant disclosure provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre.

In a further aspect, an F1 hybrid tobacco plant or other tobacco plant of the instant disclosure provides a yield selected from the group consisting of about between 1200 and 3500, between 1200 and 3400, between 1200 and 3300, between 1200 and 3200, between 1200 and 3100, between 1200 and 3000, between 1200 and 2900, between 1200 and 2800, between 1200 and 2700, between 1200 and 2600, between 1200 and 2500, between 1200 and 2400, between 1200 and 2300, between 1200 and 2200, between 1200 and 2100, between 1200 and 2000, between 1200 and 1900, between 1200 and 1800, between 1200 and 1700, between 1200 and 1600, between 1200 and 1500, and between 1200 and 1400 lbs/acre.

In one aspect, an F1 hybrid tobacco plant or other tobacco plant of the instant disclosure provides cured tobacco of commercially acceptable grade. Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast.

In one aspect, an F1 hybrid tobacco plant or other tobacco plant of the instant disclosure is male sterile. In another aspect, an F1 hybrid tobacco plant or other tobacco plant of the instant disclosure is cytoplasmic male sterile. Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp.

Either parent of an F1 hybrid can be male sterile or cytoplasmic male sterile. In one aspect, the larger-leaf parent of the F1 hybrid of the instant disclosure is male sterile or cytoplasmic male sterile. In another aspect, the flue-cured parent of the F1 hybrid of the instant disclosure is male sterile or cytoplasmic male sterile. In one aspect, the male sterile flue-cured parent is from a cytoplasmic male sterile K326 variety. In a further aspect, the Oriental parent of the F1 hybrid of the instant disclosure is male sterile or cytoplasmic male sterile.

While not limited by any scientific theory or mechanism, among leaf surface chemicals contributing to tobacco flavor and aroma characteristics, α- and β-4,8,13-duvatriene-1,3-diols (DVTs) are synthesized and excreted by glandular trichomes. See U.S. Pat. No. 8,168,855. Genotypes lacking glandular secreting trichomes appear incapable of producing anything more than trace quantities of DVTs, while genotypes with glandular trichomes may produce from 1 µg/cm$^2$ to as much as 190 µg/cm$^2$ DVTs. See Nielsen and Severson, *J. Agic. Food Chem.,* 38(2):467-71 (1990); and Nielsen and Severson, *Crop Science,* 32(5):1148-50 (1992). Furthermore, genetic analyses indicated that presence of absence of secreting trichomes was controlled by alleles at a single dominant locus. See Nielsen et al., *Crop Science,* 22(5): 1050-53 (1982).

In one aspect, the tobacco F1 hybrids of the instant disclosure comprise a trichome density similar to their corresponding Oriental parent. In another aspect, the tobacco F1 hybrids of the instant disclosure comprise a trichome density comparable to their corresponding Oriental parent. In an further aspect, the trichome density of the tobacco F1 hybrids of the instant disclosure is about between 95% to 105%, between 90% and 110%, between 85% and 115%, between 80% and 120%, between 75% and 125%, between 70% and 130%, between 65% and 135%, between 60% and 140%, or between 55% and 145% of the trichome density in a leaf of a comparable stock position from their corresponding Oriental parent. Trichome densities can be measured by counting the number of trichomes per unit leaf area.

In one aspect, an F1 hybrid tobacco plant or other tobacco plant of the instant disclosure is adapted for machine harvesting. In another aspect, an F1 hybrid tobacco plant or other tobacco plant of the instant disclosure is harvested mechanically.

An F1 hybrid tobacco plant or other tobacco plant of the instant disclosure can be grown in any region, latitude, or altitude. In one aspect, an F1 hybrid tobacco plant or other tobacco plant of the instant disclosure is adapted for growth in a latitude selected from between 60° N and 40° S, between 57.5° N and 40° S, between 55° N and 40° S, between 52.5° N and 40° S, between 50° N and 40° S, between 47.5° N and 40° S, between 45° N and 40° S, between 42.5° N and 40° S, between 40° N and 40° S, between 37.5° N and 40° S, between 35° N and 40° S, between 32.5° N and 40° S, between 30° N and 40° S, between 27.5° N and 40° S, between 25° N and 40° S, between 22.5° N and 40° S, between 20° N and 40° S, between 17.5° N and 40° S, between 15° N and 40° S, between 12.5° N and 40° S, between 10° N and 40° S, between 7.5° N and 40° S, between 5° N and 40° S, between 2.5° N and 40° S, between 2.5° S and 40° S, between 5° S and 40° S, between 7.5° S and 40° S, between 10° S and 40° S, between 12.5° S and 40° S, between 15° S and 40° S, between 17.5° S and 40° S, between 20° S and 40° S, between 22.5° S and 40° S, between 25° S and 40° S, between 27.5° S and 40° S, between 30° S and 40° S, between 32.5° S and 40° S, between 35° S and 40° S, and between 37.5° S and 40° S.

In another aspect, an F1 hybrid tobacco plant or other tobacco plant of the instant disclosure is adapted for growth in a latitude selected from between 60° N and 40° S, between 57.5° N and 37.5° S, between 55° N and 27.5° S, between 52.5° N and 25° S, between 50° N and 22.5° S, between 47.5° N and 20° S, between 45° N and 17.5° S, between 42.5° N and 15° S, between 40° N and 12.5° S, between 37.5° N and 10° S, between 35° N and 7.5° S, between 32.5° N and 5° S, between 30° N and 2.5° S, between 27.5° N and 2.5° S, between 25° N and 5° S, between 22.5° N and 7.5° S, between 20° N and 10° S, between 17.5° N and 12.5° S, and between 15° N and 10° N.

In one aspect, an F1 hybrid tobacco plant or other tobacco plant of the instant disclosure is adapted for growth in a latitude selected from between 60° N and 37.5° S, between 60° N and 35° S, between 60° N and 32.5° S, between 60° N and 30° S, between 60° N and 27.5° S, between 60° N and 25° S, between 60° N and 22.5° S, between 60° N and 20° S, between 60° N and 17.5° S, between 60° N and 15° S, between 60° N and 12.5° S, between 60° N and 10° S, between 60° N and 7.5° S, between 60° N and 5° S, between 60° N and 2.5° S, between 60° N and 2.5° N, between 60° N and 5° N, between 60° N and 7.5° N, between 60° N and 10° N, between 60° N and 12.5° N, between 60° N and 15° N, between 60° N and 17.5° N, between 60° N and 20° N, between 60° N and 22.5° N, between 60° N and 25° N, between 60° N and 27.5° N, between 60° N and 30° N, between 60° N and 32.5° N, between 60° N and 35° N, between 60° N and 37.5° N, between 60° N and 40° N, between 60° N and 42.5° N, between 60° N and 45° N, between 60° N and 47.5° N, between 60° N and 50° N, between 60° N and 52.5° N, between 60° N and 55° N, and between 60° N and 57.5° N.

In a further aspect, an F1 hybrid tobacco plant or other tobacco plant of the instant disclosure is adapted for growth in a latitude selected from the group consisting of about 60° N, 57.5° N, 55° N, 52.5° N, 50° N, 47.5° N, 45° N, 42.5° N, 40° N, 37.5° N, 35° N, 32.5° N, 30° N, 27.5° N, 25° N, 22.5° N, 20° N, 17.5° N, 15° N, 12.5° N, 10° N, 7.5° N, 5° N, 2.5° N, 2.5° S, 5° S, 7.5° S, 10° S, 12.5° S, 15° S, 17.5° S, 20° S, 22.5° S, 25° S, 27.5° S, 30° S, 32.5° S, 35° S, 37.5° S, and 40° S.

In one aspect, an F1 hybrid tobacco plant or other tobacco plant of the instant disclosure is adapted for growth in an altitude selected from between 20 and 50, between 50 and 100, between 150 and 200, between 250 and 300, between 350 and 400, between 450 and 500, between 550 and 600, between 650 and 700, between 750 and 800, between 850 and 900, between 950 and 1000, between 1050 and 1100, between 1150 and 1200, between 1250 and 1300, between 1350 and 1400, between 1450 and 1500, between 1550 and 1600, between 1650 and 1700, between 1750 and 1800, between 1850 and 1900, between 1950 and 2000, between 2050 and 2100, and between 2150 and 2200 meters.

In one aspect, an F1 hybrid tobacco plant or other tobacco plant of the instant disclosure comprises one or more Oriental aroma compounds at a concentration comparable to the concentration of the same one or more Oriental aroma compounds in the Oriental parent of the F1 hybrid, and further comprises a yield similar to the yield of the flue-cured type parent variety of the F1 hybrid when grown under similar growth conditions.

In another aspect, an F1 hybrid tobacco plant or other tobacco plant of the instant disclosure comprises one or more Oriental aroma compounds at a concentration between 75% and 125%, or between 85% and 115% of the concentrations of the same one or more Oriental aroma compounds in the Oriental parent of the F1 hybrid, and further comprises a yield between 60% and 100%, between 80% and 100%, or between 90% and 100% of the yield of the flue-cured parent of the F1 hybrid when grown in similar field conditions.

In another aspect, an F1 hybrid tobacco plant or other tobacco plant of the instant disclosure comprises one or more Oriental aroma compounds at a concentration between 75% and 125%, or between 85% and 115% of the concentrations of the same one or more Oriental aroma compounds in the Oriental parent of the F1 hybrid, and further comprises a yield approximately 1.6, 1.8, 2.0, 2.2, or 2.4 times of the yield of the flue-cured parent of the F1 hybrid when grown in similar field conditions.

In another aspect, an F1 hybrid tobacco plant or other tobacco plant of the instant disclosure comprises one or more Oriental aroma compounds selected from the group consisting of 3-methylvaleric acid, valeric acid, isovaleric acid, a labdenoid, a cembrenoid, a sugar ester, and a reducing sugar, at a concentration between 75% and 125%, or between 85% and 115% of the concentrations of the same one or more Oriental aroma compounds in the Oriental parent of the F1 hybrid, and further comprises a yield approximately 1.6, 1.8, 2.0, 2.2, or 2.4 times of the yield of the flue-cured parent of the F1 hybrid when grown in similar field conditions.

In another aspect, an F1 hybrid tobacco plant or other tobacco plant of the instant disclosure comprises 3-methylvaleric acid in cured material at a concentration between 75% and 125%, or between 85% and 115% of the concentrations of 3-methylvaleric acid in the Oriental parent of the F1 hybrid, and further comprises a yield approximately 1.6, 1.8, 2.0, 2.2, or 2.4 times of the yield of the flue-cured parent of the F1 hybrid when grown in similar field conditions.

In another aspect, an F1 hybrid tobacco plant or other tobacco plant of the instant disclosure comprises valeric acid in cured material at a concentration between 75% and 125%, or between 85% and 115% of the concentrations of valeric acid in the Oriental parent of the F1 hybrid, and further comprises a yield approximately 1.6, 1.8, 2.0, 2.2, or 2.4 times of the yield of the flue-cured parent of the F1 hybrid when grown in similar field conditions.

In another aspect, an F1 hybrid tobacco plant or other tobacco plant of the instant disclosure comprises isovaleric acid in cured material at a concentration between 75% and 125%, or between 85% and 115% of the concentrations of isovaleric acid in the Oriental parent of the F1 hybrid, and further comprises a yield approximately 1.6, 1.8, 2.0, 2.2, or 2.4 times of the yield of the flue-cured parent of the F1 hybrid when grown in similar field conditions.

In another aspect, an F1 hybrid tobacco plant or other tobacco plant of the instant disclosure comprises cis-Abienol in green leaves at a concentration between 75% and 125%, or between 85% and 115% of the concentrations of cis-Abienol in the Oriental parent of the F1 hybrid, and further comprises a yield approximately 1.6, 1.8, 2.0, 2.2, or 2.4 times of the yield of the flue-cured parent of the F1 hybrid when grown in similar field conditions.

In another aspect, an F1 hybrid tobacco plant or other tobacco plant of the instant disclosure comprises Duvatriene-diols in green leaves at a concentration between 75% and 125%, or between 85% and 115% of the concentrations of Duvatriene-diols in the Oriental parent of the F1 hybrid, and further comprises a yield approximately 1.6, 1.8, 2.0, 2.2, or 2.4 times of the yield of the flue-cured parent of the F1 hybrid when grown in similar field conditions.

In another aspect, an F1 hybrid tobacco plant or other tobacco plant of the instant disclosure comprises sugar esters in green leaves at a concentration between 75% and 125%, or between 85% and 115% of the concentrations of sugar esters in the Oriental parent of the F1 hybrid, and further comprises a yield approximately 1.6, 1.8, 2.0, 2.2, or 2.4 times of the yield of the flue-cured parent of the F1 hybrid when grown in similar field conditions.

In another aspect, an F1 hybrid tobacco plant or other tobacco plant of the instant disclosure comprises reducing sugars in cured material at a concentration between 75% and 125%, or between 85% and 115% of the concentrations of reducing sugars in the Oriental parent of the F1 hybrid, and further comprises a yield approximately 1.6, 1.8, 2.0, 2.2, or 2.4 times of the yield of the flue-cured parent of the F1 hybrid when grown in similar field conditions.

In another aspect, an F1 hybrid tobacco plant or other tobacco plant of the instant disclosure comprises nicotine in cured material at a concentration between 75% and 125%, or between 85% and 115% of the concentrations of nicotine in the Oriental parent of the F1 hybrid, and further comprise a yield approximately 1.6, 1.8, 2.0, 2.2, or 2.4 times of the yield of the flue-cured parent of the F1 hybrid when grown in similar field conditions.

In another aspect, an F1 hybrid tobacco plant or other tobacco plant of the instant disclosure comprises nicotine in cured material at a concentration selected from the group consisting of 1.2%, 1.4%, 1.6%, 1.8%, and 2%, and further comprises a yield approximately 1.6, 1.8, 2.0, 2.2, or 2.4 times of the yield of the flue-cured parent of the F1 hybrid when grown in similar field conditions.

In another aspect, an F1 hybrid tobacco plant or other tobacco plant of the instant disclosure comprises one or more traits selected from the group consisting of:

a) comprising one or more Oriental aroma compounds in green leaves selected from the group consisting of a labdenoid, a cembrenoid, and a sugar ester, at a concentration between 75% and 125%, or between 85% and 115% of the concentrations of the same one or more Oriental aroma compounds in the Oriental parent of the F1 hybrid when grown in similar field conditions, b) comprising one or more Oriental aroma compounds in cured material selected from the group consisting of 3-methylvaleric acid, valeric acid, isovaleric acid, and a reducing sugar, at a concentration between 75% and 125%, or between 85% and 115% of the concentrations of the same one or more Oriental aroma compounds in the Oriental parent of the F1 hybrid when grown in similar field conditions, c) comprising a yield between about 1200 and about 2400, between about 1400 and about 2400 or between about 1600 and about 2400 lbs/acre, d) comprising a mature plant height between about 40 and about 80 inches, e) comprising between about 18 and about 25 harvestable leaves, f) comprising cutters with a length between about 25 and about 35 inches, and g) comprising cutters with a width between about 12 and about 16 inches.

Hybrids can be produced by preventing self-pollination of female parent plants (i.e., seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility wherein a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting F1 seed is harvested.

In the instant disclosure, a female parent can be selected from the group consisting of a larger-leaf variety, a male sterile larger-leaf variety, a cytoplasmic male sterile larger-leaf variety, a flue-cured variety, a male sterile flue-cured variety, a cytoplasmic male sterile flue-cured variety, an Oriental variety, a male sterile Oriental variety, and a cytoplasmic male sterile Oriental variety. A male parent can be a larger-leaf variety, a flue-cured variety, or an Oriental variety.

In one aspect, an F1 hybrid of the instant disclosure has a female larger-leaf parent and a male Oriental parent. In another aspect, an F1 hybrid of the instant disclosure has a female Oriental parent and a male larger-leaf parent. In one aspect, an F1 hybrid of the instant disclosure has a female flue-cured parent and a male Oriental parent. In another aspect, an F1 hybrid of the instant disclosure has a female Oriental parent and a male flue-cured parent. In one aspect, the foregoing female parents are male sterile. In another aspect, the foregoing female parents are cytoplasmic male sterile.

Plants can be used to form single-cross tobacco F1 hybrids. Pollen from a male parent plant is manually transferred to an emasculated female parent plant or a female parent plant that is male sterile to form F1 seed. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed. Self-incompatibility can be used to particular advantage to prevent self-pollination of female parents when forming a double-cross hybrid.

The instant disclosure provides a method of producing an F1 hybrid, comprising crossing a larger-leaf parent tobacco plant with an Oriental parent tobacco plant and selecting an F1 hybrid. In one aspect, the selected F1 hybrid comprises one or more Oriental aroma compounds at a concentration comparable to the concentration of the same Oriental aroma compounds in the Oriental parent of the F1 hybrid when grown under similar growth conditions. In another aspect, the selected F1 hybrid tobacco plant comprises a compound selected from the group consisting of 3-methylvaleric acid, valeric acid, isovaleric acid, a labdenoid, a cembrenoid, nicotine, total sugar esters, and reducing sugars at a concentration comparable to the concentration of that compound in the Oriental parent plant of the F1 hybrid when grown under similar growth conditions. In a further aspect, the selected F1 hybrid tobacco plant comprises a trait selected from the group consisting of mature plant height, harvestable leaf number, average node length, cutter leaf length, cutter leaf width, and yield comparable to that trait in the larger-leaf parent plant of the F1 hybrid when grown under similar growth conditions.

The instant disclosure also provides a method of producing an F1 hybrid, comprising crossing a flue-cured parent tobacco plant with an Oriental parent tobacco plant and selecting an F1 hybrid. In one aspect, the selected F1 hybrid comprises one or more Oriental aroma compounds at a concentration comparable to the concentration of the same Oriental aroma compounds in the Oriental parent of the F1 hybrid when grown under similar growth conditions. In another aspect, the selected F1 hybrid tobacco plant comprises a compound selected from the group consisting of 3-methylvaleric acid, valeric acid, isovaleric acid, a labdenoid, a cembrenoid, nicotine, total sugar esters, and reducing sugars at a concentration comparable to the concentration of that compound in the Oriental parent plant of the F1 hybrid when grown under similar growth conditions. In a further aspect, the selected F1 hybrid tobacco plant comprises a trait selected from the group consisting of mature plant height, harvestable leaf number, average node length, cutter leaf length, cutter leaf width, and yield comparable to that trait in the flue-cured parent plant of the F1 hybrid when grown under similar growth conditions.

The instant disclosure also provides a method of growing an F1 hybrid plant between a larger-leaf parent plant and an Oriental parent plant, where the method comprising planting an F1 hybrid seed between a larger-leaf parent plant and an Oriental parent plant, and harvesting tobacco material from said F1 hybrid plant.

The instant disclosure also provides for breeding and progenies of an F1 hybrid tobacco plant or other tobacco plant disclosed herein. Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in a $F_2$ or backcross generation using F1 hybrid plants disclosed herein or further crossing the F1 hybrid plants with other donor plants with an agronomically desirable genotype. Plants in the $F_2$ or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. A recurrent parent in the instant disclosure can be a flue-cured variety, a Burley variety, a dark air-cured variety, a dark fire-cured variety, or an Oriental variety. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

This disclosure also includes, without limitation, breeding with other *Nicotiana* species than *Nicotiana tabacum*. Such *Nicotiana* species which exhibit breeding compatibility with *Nicotiana tabacum* include, without limitation, *Nicotiana amplexicaulis*, PI 271989; *Nicotiana benthamiana* PI 555478; *Nicotiana bigelovii* PI 555485; *Nicotiana debneyi; Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica; Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572. See also, Compendium of Tobacco Diseases published by American Phytopathology Society, or The Genus *Nicotiana* Illustrated, published by Japan Tobacco Inc, hereby incorporated by reference in their entirety.

Results of a plant breeding program using the tobacco plants described herein includes useful lines, cultivars, varieties, progeny, inbreds, and hybrids of the instant disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A "line" as distinguished from a variety most often denotes a group of plants used non-commercially, for example in plant research. A line typically displays little overall variation between individuals for one or more traits of interest, although there may be some variation between individuals for other traits.

An additional aspect of the instant disclosure provides a method for producing a tobacco plant that contains in its nuclear DNA one or more transgenes, comprising crossing a plant disclosed in the instant disclosure with a second plant containing one or more transgenes wherein progeny are produced, so that the nuclear DNA of the progeny that result from the cross comprise the transgene(s) optionally operably linked to one or more regulatory elements.

The instant disclosure further provides for the vegetative propagation of a plant disclosed herein. In one aspect, the instant disclosure provides for a method of vegetatively propagating a plant of a tobacco cultivar comprising collecting tissue capable of being propagated, cultivating the tissue to obtain a proliferated shoot and rooting the proliferated shoots to obtain a rooted plantlet.

A plant disclosed herein may be further bred by mutagenesis followed by selecting or screening the mutagenized plant material, or progeny thereof. Such screening and selection methodologies are known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

It is understood that any tobacco plant of the instant disclosure can be transformed by a genetic construct or transgene using a technique known in the art. Without limitation, an example of a desired trait is herbicide resistance, pest resistance, disease resistance; high yield; high grade index; curability; curing quality; mechanical harvestability; holding ability; leaf quality; height, plant maturation (e.g., early maturing, early to medium maturing, medium maturing, medium to late maturing, or late maturing); stalk size (e.g., a small, medium, or a large stalk); or leaf number per plant (e.g., a small (e.g., 5-10 leaves), medium (e.g., 11-15 leaves), or large (e.g., 16-21) number of leaves), or any combination. Any plant of the instant disclosure can be used as a basis for tissue culture, transformed, or a combination of any of these. In an aspect, a plant of the instant disclosure derived by tissue culture, transformation, or both has essentially all of the morphological and physiological characteristics of initial cultivar.

The instant disclosure further provides cured tobacco material, tobacco blends, and tobacco products made from tobacco plants disclosed herein. In one aspect, the cured tobacco material of the instant disclosure is sun-cured. In another aspect, the cured tobacco material of the instant disclosure is flue-cured, air-cured, or fire-cured.

Tobacco material obtained from the tobacco lines, varieties or hybrids of the instant disclosure can be used to make tobacco products including, without limitation, cigarette products (e.g., cigarettes and bidi cigarettes), cigar products (e.g., cigar wrapping tobacco and cigarillos), pipe tobacco products, products derived from tobacco, tobacco-derived nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, and the like. See, e.g., U.S. Patent Publication No. US 2006/0191548, which is herein incorporated by reference in its entirety.

Tobacco products derived from plants of the instant disclosure also include cigarettes and other smoking articles, particularly those smoking articles including filter elements, wherein the rod of smokable material includes cured tobacco within a tobacco blend. In an aspect, a tobacco product of the instant disclosure is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the instant disclosure is a smokeless tobacco product. In a further aspect, a tobacco product of the instant disclosure is selected from the group consisting of loose leaf chewing tobacco, plug chewing tobacco, moist snuff, and nasal snuff In yet another aspect, a tobacco product of the instant disclosure is selected from the group consisting of an electronically heated cigarette, an e-cigarette, an electronic vaporing device.

In an aspect, a tobacco product of the instant disclosure can be a blended tobacco product. In another aspect, a tobacco product of the instant disclosure can be a low nicotine tobacco product. In a further aspect, a tobacco product of the instant disclosure may comprise nornicotine at a level of less than about 3 mg/g. For example, the nornicotine content in such a product can be 3.0 mg/g, 2.5 mg/g, 2.0 mg/g, 1.5 mg/g, 1.0 mg/g, 750 μg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable.

In an aspect, a tobacco product prepared from an F1 hybrid tobacco plant or other tobacco plant of the instant disclosure can have a flavor similar to or indistinguishable from a tobacco product prepared with the Oriental parent of the F1 hybrid.

In one aspect, a tobacco blend product of the instant disclosure comprises at least about 5, 10, 20, 30, 40, 50, 60, 70, 80, 90, or 95 percent by dry weight of tobacco cured from F1 hybrid plants of the instant disclosure. US 2008/0245377 is herein incorporated by reference for blend mixtures in its entirety. In another aspect, a tobacco blend product of the instant disclosure comprises by dry weight tobacco material prepared from F1 hybrid plants of the instant disclosure at a ratio between 25% and 30%, between 25% and 35%, between 25% and 40%, between 25% and 45%, between 25% and 50%, between 30% and 45%, between 35% and 40%, between 30% and 50%, between 35% and 50%, between 45% and 50%, or between 45% and 50%.

The instant disclosure further provides a method manufacturing a tobacco product, where the method comprising conditioning aged tobacco material made from an F1 hybrid tobacco plant or other tobacco plant disclosed herein to increase its moisture content from between about 12.5% and about 13.5% to about 21%, blending the conditioned tobacco material to produce a desirable blend. In one aspect, the method of manufacturing a tobacco product disclosed herein further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

In one aspect, this application provides tobacco plant cells, tissues, and organs that are not reproductive material and do not mediate the natural reproduction of the plant. In another aspect, this application also provides tobacco plant cells, tissues, and organs that are reproductive material and mediate the natural reproduction of the plant. In another aspect, this application provides tobacco plant cells, tissues, and organs that cannot maintain themselves via photosynthesis. In another aspect, this application provides somatic tobacco plant cells. Somatic cells, contrary to germline cells, do not mediate plant reproduction.

The provided cells, tissues and organs may be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, vascular tissue. In another aspect, this application provides a tobacco plant chloroplast. In a further aspect, this application provides epidermal cells, stomata cell, leaf or root hairs, a storage root, or a tuber. In another aspect, this application provides a tobacco protoplast.

Skilled artisans understand that tobacco plants naturally reproduce via seeds, not via asexual reproduction or vegetative propagation. In one aspect, this application provides tobacco endosperm. In another aspect, this application provides tobacco endosperm cells. In a further aspect, this application provides a triploid plant that cannot reproduce sexually or produce seeds. In another aspect, this application provides a male or female sterile tobacco plant, which cannot reproduce without human intervention. In another aspect, this application provides a male or female sterile tobacco plant, which cannot reproduce without human intervention.

Having now generally described the disclosure, the same will be more readily understood through reference to the following examples that are provided by way of illustration, and are not intended to be limiting of the instant disclosure, unless specified.

Each and every U.S. or foreign patent, publication of patent application, non-patent literature or any other reference mentioned in this application is incorporated by reference in its entirety.

EXAMPLES

Example 1: Preparation of F1 Hybrid Tobacco Between Larger-Leaf Type Tobacco and Oriental Type Tobacco Thirty five F1 hybrids were developed between seven Oriental tobacco parent varieties and five larger-leaf tobacco parent varieties (Table 1). The seven Oriental tobacco parent varieties used were Basma, Katerini S53, Izmir Ego 64, Xanthi Yaka NO 18A, Trapezund 161, TI 1253, and TI 1302. Five larger-leaf tobacco parent varieties used as male parents were K326, TN 90 LC, Maryland 609, TI 1068, and KDH-960.

F1 hybrids were selected for Oriental tobacco characteristics based on their cured leaf chemistry profile and hyperspectral imaging which were compared to chemistry and imaging data from commercial Oriental tobacco types. Levels of cis-Abienol (a representative labdenoid), Duvatriene-diols (a representative cembrenoid), and total esters (III to V) derived from C3 to C5 carboxylic acids) were measured in green leaves. Green leaves were collected at maturity from the fourth to fifth stock position from the top in serial harvesting. Levels of isovaleric acid, 3-methyl-valeric acid, nicotine, and reducing sugars were measured from leaves following sun-curing. Table 1 lists chemistry profiling data collected from Oriental and larger-leaf tobacco parent varieties as well as the thirty five F1 hybrids.

Example 2: Profiling of Tobacco Leaf Chemistry by GC-Mass Spectrometry

An exemplary illustration of evaluating aroma in Oriental tobaccos based on valeric acid gas chromatography is shown in Dagnon et al., *Contributions to Tobacco Research*, 23(2): 115-20 (2008), which reference is incorporated by reference in its entirety. A further illustration can be found in Dagnon et al., Chemometric Evaluation of the Colour and Smoke Aroma in Oriental Tobaccos Based on the Polyphenol and Valeric Acid Cultivar Characteristics as Influenced by the Genotype, *Bulgarian Journal of Argricultrual Science*, 13:459-466 (2007).

Example 3: Sun-Curing of F1 Hybrid and Oriental Tobaccos

Tobacco F1 hybrids of the instant disclosure and their Oriental parents are cured in sunlight following the general practice outlined by Antoniou and Skendrou in MANUAL OF GOOD AGRICULTURE PRACTICES FOR ORIENTAL TOBACCO, English Translation Issued by SEKE S. A. in May 2004). In general, the sun-curing process takes place under specific conditions of temperature, humidity and aeration, which leads to a progressive loss of water from tobacco leaves. Three stages of curing include (1) yellowing phase during which an even and slow loss of water from leaves is sought, and the leaves wither and the lamina turns yellow due to destruction of the chlorophyll; (2) stabilizing or color-setting phase during which a complete loss of water from the leaves is achieved, and the leaves acquire their dominant color; and (3) vein-drying phase during which the stem (mid-rib) and veins of the leaf are completely dried. The length of curing is influenced by a number of factors including, but not limited to, ambient weather conditions (e.g., temperature, sunshine, relative humidity, rain, and wind), tobacco varieties, leaf stalk positions, the degree of leaf ripeness at reaping, leaf stringing densities, and stringing methods.

Example 4: Hyperspectral Imaging of Tobacco Leaves

Exemplary results obtained from hyperspectral imaging of sun-cured tobacco leaves of different varieties in comparison to Burley, flue-cured, and Oriental tobaccos are illustrated in FIG. 1. Methods for hyperspectral imaging can be found in U.S. Provisional Patent Application, Ser. No. 61/728,123, filed on Nov. 19, 2012 and entitled "BLENDING OF AGRICULTURAL PRODUCTS VIA HYPERSPECTRAL IMAGING AND ANALYSIS" (which is a priority filing to PCT Application PCT/US13/70814 filed Nov. 19, 2013), which PCT and provisional are herein incorporated by reference in their entireties.

Example 5: Selection, Development, and Field Testing of High Yielding Tobacco F1 Hybrids with Oriental Tobacco Characteristics Among the 35 F1 hybrids (see Table 1), three F1 hybrids, K326×Izmir Ego 64, K326×Katerini S53 and K326×Basma, have cured leaf chemistry profiles and hyperspectral imaging similar to their respective Oriental parent. These three F1 hybrids also comprise flavors that most closely resemble their Oriental parent according to expert smoke panel evaluations. A general description of tobacco flavoring evaluations can be found in *Tobacco Production, Chemistry and Technology*, Edited by L. Davis and M. Nielsen, Blackwell Science, 1999.

Example 6: Development of Male Sterile High Yielding Tobacco F1 Hybrids with Oriental Tobacco Characteristics Three Oriental tobacco parent varieties Basma, Katerini S53, and Izmir Ego 64 were crossed as the pollen parent to a male sterile line of flue-cured variety K326 ("MS K326"). The resulting F1 hybrids (e.g., MS K326×Izmir Ego 64, MS K326×Katerini S53 and MS K326×Basma) are male sterile high yielding hybrids with Oriental tobacco characteristics.

DEPOSIT INFORMATION

A deposit of at least 2500 seeds of parent varieties of tobacco hybrids disclosed above and recited in the appended claims have been made with American Type Culture Collection (ATCC), 10801 University Boulevard, Manassas, Va. 20110. The date of deposit for seeds representative of varieties MS K326, Izmir Ego 64, Katerini S53, and Basma was Oct. 30, 2013, on behalf of Altria Client Services Inc. The deposit of 2500 seeds for each variety were taken from the same deposit maintained since prior to the filing date of this disclosure. Upon issuance of a patent, all restrictions upon the deposit will be removed, and the deposit is intended to meet all of the requirements of 37 C.F.R. § 1.801-1.809. The ATCC accession numbers for seeds representative of varieties MS K326, Izmir Ego 64, Katerini S53, and Basma are, respectively, PTA-120686, PTA-120684, PTA-120685, PTA-120683. These deposits will be maintained in the depository for a period of 30 years, or 5 years after the last request, or for the effective life of the patent, whichever is longer, and will be replaced as necessary during that period. Applicants do not waive any infringement of their rights granted under this patent or under the Plant Variety Protection Act (7 U.S.C. 2321 et seq.).

TABLE 1

Leaf chemistry profiling data from 35 F1 hybrids and larger-leaf parent tobacco varieties (K326, TN 90 LC, Maryland 609, TI 1068, and KDH-960) and Oriental type parent tobacco varieties (Basma, Katerini S53, Izmir Ego 64, Xanthi Yaka NO 18A, Trapezund 161, TI1253, and TI 1302).

| Variety/Hybrid | Tobacco Type | cis-Abienol | Total Esters (III to V) | Duvatriene-diols | Isovaleric Acids (µg/g) | 3-Methyl-valeric Acids (µg/g) | Nicotine (%) | Reducing Sugars (%) |
|---|---|---|---|---|---|---|---|---|
| K326 | Flue-cured | 0 | 20 | 258 | 363 | 217 | 0.8 | 16.8 |
| TN 90 LC | Burley | 0 | 0 | 473 | 395 | 69 | 1.5 | 5.8 |
| Maryland 609 | Maryland | 0 | 0 | 306 | 400 | 255 | 1.5 | 11.8 |
| TI 1068 | Other | 38 | 119 | 501 | 1350 | 6201 | 1.4 | 1.7 |
| KDH-960 | Burley | 0 | 0 | 442 | 1125 | 40 | 1.7 | 4.1 |
| Basma | Oriental | 43 | 49 | 152 | 586 | 1662 | 2.0 | 8.2 |
| Katerini S53 | Oriental | 0 | 10 | 412 | 448 | 1777 | 1.1 | 20.0 |
| Izmir Ego 64 | Oriental | 55 | 13 | 253 | 316 | 934 | 0.0 | 19.6 |
| Xanthi Yaka NO 18A | Oriental | 25 | 19 | 342 | 793 | 2257 | 2.2 | 1.5 |
| Trapezund 161 | Oriental | 31 | 19 | 132 | 801 | 1945 | 2.1 | 4.1 |
| TI 1253 | Oriental | 9 | 21 | 238 | 900 | 3486 | 2.5 | 1.8 |
| TI 1302 | Oriental | 0 | 9 | 228 | 673 | 3602 | 1.2 | 21.1 |
| K326 × Basma | Hybrid | 35 | 154 | 515 | 396 | 1552 | 1.2 | 9.8 |
| K326 × Katerini S53 | Hybrid | 0 | 58 | 658 | 403 | 1614 | 0.0 | 16.7 |
| K326 × Izmir Ego 64 | Hybrid | 42 | 75 | 549 | 409 | 827 | 0.8 | 12.2 |
| K326 × Xanthi Yaka NO 18A | Hybrid | 14 | 43 | 459 | 487 | 1752 | 1.6 | 9.5 |
| K326 × Trapezund 161 | Hybrid | 9 | 22 | 262 | 562 | 1627 | 1.0 | 7.6 |
| K326 × TI1253 | Hybrid | 10 | 37 | 363 | 512 | 1865 | 1.5 | 5.1 |
| K326 × TI 1302 | Hybrid | 0 | 34 | 453 | 1008 | 4188 | 1.1 | 5.6 |
| TN 90 LC × Basma | Hybrid | 18 | 15 | 452 | 309 | 990 | 0.0 | 16.2 |
| TN 90 LC × Katerini S53 | Hybrid | 0 | 0 | 343 | 424 | 1268 | 1.5 | 14.6 |
| TN 90 LC × Izmir Ego 64 | Hybrid | 22 | 15 | 608 | 480 | 960 | 1.3 | 11.2 |
| TN 90 LC × Xanthi Yaka NO 18A | Hybrid | 12 | 15 | 497 | 537 | 1586 | 1.2 | 14.1 |

TABLE 1-continued

Leaf chemistry profiling data from 35 F1 hybrids and larger-leaf parent tobacco
varieties (K326, TN 90 LC, Maryland 609, TI 1068, and KDH-960) and Oriental type parent
tobacco varieties (Basma, Katerini S53, Izmir Ego 64, Xanthi Yaka NO 18A, Trapezund 161,
TI1253, and TI 1302).

| Variety/Hybrid | Tobacco Type | cis-Abienol | Total Esters (III to V) | Duvatriene-diols | Isovaleric Acids (μg/g) | 3-Methyl-valeric Acids (μg/g) | Nicotine (%) | Reducing Sugars (%) |
|---|---|---|---|---|---|---|---|---|
| TN 90 LC × Trapezund 161 | Hybrid | 12 | 14 | 366 | 699 | 1592 | 1.2 | 7.8 |
| TN 90 LC × TI1253 | Hybrid | 22 | 42 | 416 | 387 | 1223 | 1.5 | 12.0 |
| TN 90 LC × TI 1302 | Hybrid | 0 | 47 | 692 | 459 | 1714 | 0.9 | 12.9 |
| Maryland 609 × Basma | Hybrid | 20 | 31 | 327 | 389 | 1166 | 1.5 | 12.4 |
| Maryland 609 × Katerini S53 | Hybrid | 0 | 16 | 572 | 419 | 1216 | 2.0 | 7.6 |
| Maryland 609 × Izmir Ego 64 | Hybrid | 12 | 0 | 405 | 391 | 630 | 1.1 | 17.3 |
| Maryland 609 × Xanthi Yaka NO 18 A | Hybrid | 9 | 15 | 432 | 511 | 1580 | 1.9 | 9.1 |
| Maryland 609 × Trapezund 161 | Hybrid | 9 | 15 | 316 | 449 | 1031 | 1.7 | 13.5 |
| Maryland 609 × TI1253 | Hybrid | 12 | 36 | 304 | 534 | 2024 | 0.9 | 10.2 |
| Maryland 609 × TI 1302 | Hybrid | 0 | 36 | 568 | 597 | 2167 | 1.2 | 13.3 |
| TI 1068 × Basma | Hybrid | 85 | 302 | 493 | 1091 | 4559 | 1.5 | 5.6 |
| TI 1068 × Katerini S53 | Hybrid | 25 | 154 | 688 | 940 | 3640 | 1.6 | 3.9 |
| TI 1068 × Izmir Ego 64 | Hybrid | 94 | 146 | 522 | 1162 | 4837 | 0.8 | 0.6 |
| TI 1068 × Xanthi Yaka NO 18A | Hybrid | 58 | 92 | 485 | 1123 | 4483 | 1.8 | 3.8 |
| TI 1068 × Trapezund 161 | Hybrid | 31 | 36 | 262 | 1422 | 4224 | 1.9 | 1.9 |
| TI 1068 × TI 1253 | Hybrid | 28 | 40 | 385 | 1106 | 4656 | 2.3 | 1.6 |
| TI 1068 × TI 1302 | Hybrid | 32 | 108 | 646 | 1267 | 5751 | 1.4 | 7.0 |
| KDH-960 × Basma | Hybrid | 16 | 11 | 412 | 791 | 1710 | 1.4 | 8.2 |
| KDH-960 × Katerini S53 | Hybrid | 0 | 29 | 759 | 735 | 1960 | 1.6 | 5.2 |
| KDH-960 × Izmir Ego 64 | Hybrid | 6 | 0 | 332 | 905 | 1202 | 0.0 | 9.8 |
| KDH-960 × Xanthi Yaka NO 18A | Hybrid | 7 | 10 | 433 | 1510 | 3069 | 1.0 | 4.6 |
| KDH-960 × Trapezund 161 | Hybrid | 16 | 15 | 445 | 1365 | 2597 | 1.2 | 8.1 |
| KDH-960 × TI1253 | Hybrid | 23 | 42 | 702 | 1253 | 3665 | 1.1 | 2.6 |
| KDH-960 × TI 1302 | Hybrid | 0 | 44 | 639 | 905 | 3056 | 0.9 | 15.5 |

The invention claimed is:

1. A hybrid tobacco plant, or part thereof, having a larger leaf parent plant and an oriental type parent plant, wherein said oriental type parent plant is selected from the group consisting of Basma, Katerini S53, and Izmir Ego 64, wherein a representative sample of seed of said oriental type parent Basma has been deposited under ATCC Accession No. PTA-120683, wherein a representative sample of seed of said oriental type parent Katerini S53 has been deposited-under ATCC Accession No. PTA-120685, and wherein a representative sample of seed of said oriental type parent Izmir Ego 64 has been deposited-under ATCC Accession No. PTA-120684.

2. The hybrid tobacco plant, or part thereof, of claim 1, wherein said larger leaf parent plant is selected from the group consisting of Flue-Cured tobacco, Maryland tobacco, and Burley tobacco.

3. The hybrid tobacco plant, or part thereof, of claim 2, wherein said larger leaf parent plant is selected from the group consisting of MD-609, TN90 LC, KDH-960, and K326.

4. The hybrid tobacco plant, or part thereof, of claim 1, wherein said hybrid tobacco plant comprises a yield between 1400 and 3000 pounds (lbs)/acre.

5. The hybrid tobacco plant, or part thereof, of claim 1, wherein said hybrid tobacco plant comprises one or more oriental compounds at a concentration between 50% and 150% of the concentration for the same one or more oriental compounds in said oriental type parent plant when grown in similar growth conditions, wherein said one or more oriental compounds are selected from the group consisting of 3-methylvaleric acid, valeric acid, isovaleric acid, a labdenoid, cembranoid, and a sugar ester.

6. The hybrid tobacco plant, or part thereof, of claim 1, wherein said part is selected from the group consisting of a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast.

7. A population of the hybrid tobacco plants of claim 1.

8. The population of hybrid tobacco plants of claim 7, wherein said population of hybrid tobacco plants comprises one or more compounds at an average concentration between 50% and 150% of the average concentration of said one or more compounds in said oriental type parent variety when grown in similar-growth conditions, and wherein said one or more aroma compounds are selected from the group consisting of 3-methylvaleric acid, valeric acid, isovaleric acid, a labdenoid, and a sugar ester.

9. The population of hybrid tobacco plants of claim 8, wherein the level of said labdenoid is measured from a green leaf, and wherein the levels of said 3-methylvaleric acid, valeric acid, and isovaleric acid are measured from a cured tobacco leaf.

10. The population of hybrid tobacco plants of claim 7, said population of hybrid tobacco plants comprises a yield at least 1.6 times of the yield of said oriental type parent variety when grown in similar field conditions.

11. The population of hybrid tobacco plants of claim 7, said population of hybrid tobacco plants comprises a yield between 1400 and 3000 lbs/acre.

12. The population of hybrid tobacco plants of claim 7, said population of hybrid tobacco plants is male sterile.

13. Cured tobacco material made from the hybrid tobacco plants of claim 1.

14. The cured tobacco material of claim 13, wherein said hybrid tobacco plant is sun cured.

15. A tobacco blend comprising said cured tobacco material of claim claim 13.

16. The tobacco blend of claim 15, wherein between 25% and 50% of said tobacco blend comprises said hybrid tobacco plants.

17. A tobacco product comprising said cured tobacco material of claim 13.

18. The tobacco product of claim 17, wherein said product is selected from the group consisting of a cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, shredded tobacco, and cut tobacco.

19. A method of manufacturing a tobacco product, said method comprising:
conditioning aged tobacco material made from the hybrid tobacco plant of claim 1 to increase its moisture content from between 12.5% and 13.5% to 21%, and casing or flavoring said conditioned tobacco material.

20. The hybrid tobacco plant, or part thereof, of claim 1, wherein said plant provides cured tobacco of commercially acceptable grade.

* * * * *